(12) United States Patent
Cuberes Altisen et al.

(10) Patent No.: US 7,524,868 B2
(45) Date of Patent: *Apr. 28, 2009

(54) SUBSTITUTED PYRAZOLINE COMPOUNDS, THEIR PREPARATION AND USE AS MEDICAMENTS

(75) Inventors: Rosa Cuberes Altisen, Barcelona (ES); Jordi Frigola Constansa, Barcelona (ES); Sergio Erill Saez, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 482 days.

This patent is subject to a terminal disclaimer.

(21) Appl. No.: 11/169,155

(22) Filed: Jun. 27, 2005

(65) Prior Publication Data

US 2006/0020010 A1    Jan. 26, 2006

Related U.S. Application Data

(63) Continuation-in-part of application No. 10/804,534, filed on Mar. 19, 2004, now abandoned.

(30) Foreign Application Priority Data

Feb. 17, 2004   (ES)   ............................. 200400378

(51) Int. Cl.
*A61K 31/4155* (2006.01)
*C07D 401/02* (2006.01)
(52) U.S. Cl. .................... 514/326; 546/211
(58) Field of Classification Search ................ 514/406, 514/402, 326; 548/379.4, 364.1, 362.5; 546/211
See application file for complete search history.

(56) References Cited

U.S. PATENT DOCUMENTS

| | | | |
|---|---|---|---|
| 5,017,596 A | 5/1991 | Colombo et al. | |
| 5,624,941 A * | 4/1997 | Barth et al. ................. | 514/326 |
| 5,849,931 A | 12/1998 | Frigola-Constansa et al. | |
| 6,118,009 A | 9/2000 | Torrens-Jover et al. | |
| 6,187,930 B1 | 2/2001 | Torrens-Jover et al. | |
| 6,410,582 B1 | 6/2002 | Merce-Vidal et al. | |
| 6,476,060 B2 | 11/2002 | Lange et al. | |
| 6,509,367 B1 | 1/2003 | Martin et al. | |
| 6,610,737 B1 | 8/2003 | Garzon et al. | |
| 6,956,033 B2 | 10/2005 | Ogawa et al. | |
| 7,235,574 B2 | 6/2007 | Bossenmaier et al. | |
| 2001/0053788 A1* | 12/2001 | Lange et al. ................. | 514/333 |
| 2002/0058816 A1 | 5/2002 | Kordik et al. | |
| 2002/0156104 A1 | 10/2002 | Adams et al. | |
| 2003/0022925 A1 | 1/2003 | Merce-Vidal et al. | |
| 2003/0153569 A1 | 8/2003 | Adams et al. | |
| 2004/0092535 A1 | 5/2004 | Barsanti et al. | |
| 2004/0248944 A1 | 12/2004 | Kruse et al. | |
| 2005/0137251 A1 | 6/2005 | Garzon et al. | |
| 2005/0171179 A1* | 8/2005 | Lange et al. ................. | 514/406 |
| 2005/0222138 A1 | 10/2005 | Ohhata et al. | |
| 2005/0282798 A1 | 12/2005 | Lazzari et al. | |
| 2006/0015198 A1 | 1/2006 | Okabayashi et al. | |
| 2006/0020010 A1 | 1/2006 | Altisen et al. | |
| 2006/0052315 A1 | 3/2006 | Leung et al. | |
| 2006/0106014 A1 | 5/2006 | Boddupalli et al. | |
| 2006/0128673 A1 | 6/2006 | Firnges et al. | |
| 2006/0172019 A1 | 8/2006 | Ralston et al. | |
| 2006/0189658 A1 | 8/2006 | Altisen et al. | |
| 2006/0194843 A1 | 8/2006 | Berdini et al. | |
| 2007/0015810 A1 | 1/2007 | Cuberes | |
| 2007/0015811 A1 | 1/2007 | Cuberes | |
| 2007/0021398 A1 | 1/2007 | Torrens et al. | |
| 2007/0066651 A1 | 3/2007 | Cuberes-Altisen et al. | |
| 2007/0073056 A1 | 3/2007 | Torrens et al. | |
| 2008/0015198 A1 | 1/2008 | Cuberes-Altisen et al. | |

FOREIGN PATENT DOCUMENTS

| | | |
|---|---|---|
| DE | 3540934 | 5/1987 |
| EP | 1 384 477 | 1/2004 |
| GB | 1 209 326 | 10/1970 |
| WO | WO 88/05046 A2 | 7/1988 |
| WO | WO 88/06583 | 7/1988 |
| WO | WO 92/03421 | 3/1992 |
| WO | WO 88/06583 | 9/1998 |
| WO | WO 00/76503 A1 | 12/2000 |
| WO | WO 01/70700 | 6/2001 |
| WO | WO 02/080909 | 10/2002 |
| WO | WO 02/080909 A1 | 10/2002 |
| WO | WO 03/026647 | 4/2003 |
| WO | WO 2004/060882 A1 | 7/2004 |
| WO | WO 2004/078261 A1 | 9/2004 |

(Continued)

OTHER PUBLICATIONS

Chan et al., "N-substituted Pyrazoline-type Insecticides" ACS Symposium Series, No. 800, pp. 144-155 (2002).

Hough, L.B. et al. "Inhibition of Improgan Antinociception by the Cannabinoid (CB) (1) Antagonist N-(piperidin-1-yl)-5-(4-chlorophenyl)-1(2,4-dichlorophenyl)-4-methyl-1H-pyarzole-3-carboxamide (SR141716A): Lack of Obligatory Role for Endocannabinoids Acting at CB(1) Receptors" Journal of Pharmacology and Experimental Therapeutics vol. 303, No. 1 pp. 314-322 (2002).

Hurst Dow P., et al. "N-(piperidin-1-yl)-5-(4-chlorophenyl)-1-(2,4-dichlorophenyl)-4-methyl-1H-pyrazole-3-caboxamide (SR141716A) interaction with LYS 3.28(192) is Crucial for its Inverse Agonism at the Cannabinoid CB1 Receptor" Molecular Pharmacology vol. 62, No. 6 pp. 1274-1287 (2002).

Joong-Youn, Shim et al. "Molecular Interaction of the Antagonist N-(piperidin-1-yl)-5-(4-chlorophenyl)-1-(2,4-dicholorophenyl)-4-methyl-1H-pyrazole-3-carboxamide with the CB1 Cannabinoid Receptor" Journal of Medical Chemistry, vol. 45 No. 7, pp. 144-1459 (2002).

(Continued)

*Primary Examiner*—Kamal A Saeed
*Assistant Examiner*—Kristin Bianchi
(74) *Attorney, Agent, or Firm*—Banner & Witcoff, Ltd

(57) ABSTRACT

The present invention relates to substituted pyrazoline compounds, methods for their preparation, medicaments comprising these compounds as well as their use for the preparation of a medicament for the treatment of humans and animals.

3 Claims, 2 Drawing Sheets

FOREIGN PATENT DOCUMENTS

Figure 1:
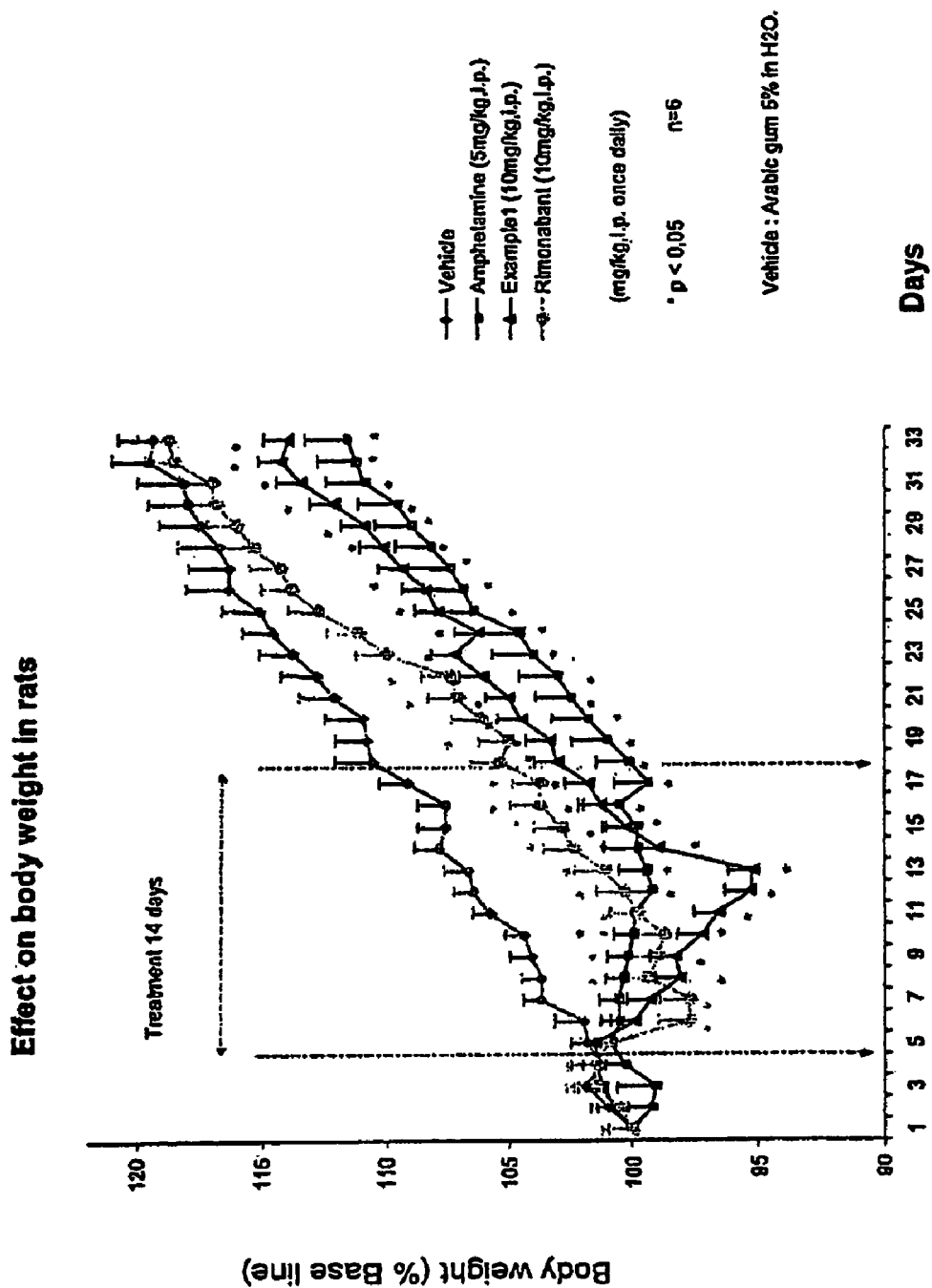

| WO | WO 2005/012256 | 2/2005 |
| --- | --- | --- |
| WO | WO 2006/045799 | 5/2006 |
| WO | WO 2006/077414 A1 | 7/2006 |
| WO | WO 2006/077419 A1 | 7/2006 |
| WO | WO 2006/077425 A1 | 7/2006 |
| WO | WO 2006/077428 A1 | 7/2006 |

OTHER PUBLICATIONS

Lan, R. et al. "Structure-Activity Relationships of Pyrazole Derviatives as Cannabinoid Receptor Antagonists" Journal of Medicinal Chemistry, vol. 42 No. 4, pp. 769-776 (1999).
Lange, J.H.M. et al., "3,4-diarylpyrozolines as Cannabinoid CB SUB 1 receptor Antagonists with Lower Lipophilicity," Bioorganic & Medicinal Chemistry Letters, vol. 15, No. 21, pp. 4794-4798 (2005).
Megard et al. "A Co-Culture Based Model of Human Blood-Brain Barrier: Application to Active Transport of Indinavire and In-Vivo-in-Vitro Correlation", Brain Research vol. 927, pp. 153-167, (2002).
Meier et al. "Insecticidal Dihydropyrazoles with Reduced Lipophilicity" ACS Symposium Series No. 504 pp. 313-326 (1992).
Meschler J.P et al. "Inverse Agonist Properties of N-(piperidin-1-yl)-5-(4-chlorophenyl)-1-(2, dichlorophenyl)-4-cyano-5-(4-methoxyphenyl)-1H-pyrazole-3-carboxylic acid phenlamide (CP 272871) for CB1 Cannabinoid Receptor" Biochemical Pharmacology vol. 60 pp. 1315-1323 (2000).
Meyer et al., "1,5-Diaryl-2,3-Pyrrolidinediones—Phenylhydrazine Derivatives" Journal of Organic Chemistry. vol. 22: pp. 1565-1567 (1957).
Muccioli, G.G. et al., "Latest Advances in Cannabinoid Receptor Antagonists and Inverse Agonists," Expert Opinion on Therapeutic Patents, vol. 16, No. 10, pp. 1405-1423 (2006).
Thomas, B.F. et al., "Synthesis of Long-chain Amide Analogs of the Cannabinoid CB1 Receptor Antagonist N-(piperidinyl)-5-(4-chlorophenyl)-1-(2,4-dichlorophenyl)-4-methyl-1H-pyrazole-3-carboxamide,(SR141716) with Unique Binding Selectives and Pharmacological Activities" Bioorganic & Medicinal Chemistry, vol. 13, No. 18, pp. 5463-5474 (2005).
Wiley, J.L. et al. "Novel Pyralzole Cannabinoids: Insights into CB(1) Receptor Recognition and Activation" Journal of Pharmacology and Experimental Therapeutics, vol. 296, No. 3, pp. 1013-1022 (2001).
Zips et al. "New Anticancer Agents: In-Vitro and In-Vivo" In Vivo vol. 19, pp. 1-7 (2005).
Hollister, L. E., "Health Aspects of Cannabis," Pharmacological Reviews, vol. 38, No. 1, pp. 1-20 (1986).
Seth, Renu et al., "Progress in Drug Research," Chemistry and Pharmacology of Cannabis, vol. 36, pp. 71-114 (1991).
Murphy, L. et al., Consroe and Sandyk, "Potential Role of Cannabinoids for Therapy of Neurological Disorders," pp. 459-524, CRC Press (1992).
Slavinska, V. et al., "New Way for the Preparation of 4-Phenyl-2-Oxobutyric Acid Ethyl Ester," Synthetic Communications, 26(11), 2229-2233 (1996).

Dujardin, G. et al., "A Straightforward Route to E-γ-Aryl-α-oxobutenoic Esters by One-step Acid-catalysed Crotonisation of Pyruvates," Synlett, No. 1, pp. 147-149 (2001).
Pascual, Alfons, "Synthese des 5-[(Acetylhydrazono)-(4-chlorphenyl)-methyl]thiophen-2-yl-esters der Trifluormethansulfonsäure," J. Prakt. Chem. 341, No. 7, pp. 695-700 (1999).
Lin, S. et al., "Regioselective Friedel-Crafts Acylation with Unsymmetrically Substituted Furandicarboxylic Acid Anhydride and Furan Acid Chloride: Syntheses of 4-Substituted 3-Arylcarbonyl-2-Phenylfuran and 3-Substituted 4-Arylcarbonyl-2-Phenylfuran," Heterocycles, vol. 55, No. 2, pp. 265-277 (2001).
Rao, P. D. et al., "Rational Syntheses of Porphyrins Bearing up to Four Different Meso Substituents," J. Org. Chem., 65, pp. 7323-7344 (2000).
Pearson, D.E. and Buehler, C.A., "Friedel-Crafts Acylations with Little or No Catalyst," Synthesis, No. 10: October, pp. 533-542 (1972).
Ross, Ruth A. et al., "Agonist-inverse agonist characterization at $CB_1$ and $CB_2$ cannabinoid receptors of L-759633, L759656 and AM630," British Journal of Pharmacology 126, pp. 665-672 (1999).
Howlett, A.C. et al., "International Union of Pharmacology XXVII. Classification of Cannabinoid Receptors," Pharmacological Reviews 54:161-202 (2002).
Compton, David R. et al., "In-Vivo Characterization of a Specific Cannabinoid Receptor Antagonist (SR141716A): Inhibition of $\Delta^9$-Tetrahydrocannabinol-Induced Responses and Apparent Agonist Activity," The Journal of Pharmacology and Experimental Therapeutics, vol. 277, No. 2, 277:586-594 (1996).
Woolfe G. et al., "The Evaluation of the Analgesic Action of Pethidine Hydrochloride (Demerol)," The Journal of Pharmacology and Experimental Therapeutics, vol. 80, pp. 300-307 (1944).
Desmedt L.K.C. et al. "Anticonvulsive Properties of Cinnarizine and Flunarizine in Rats and Mice," Arzneim.-Forsch. (Drug Res.) 25, Nr. 9, pp. 1408-1413 (1975).
G. Colombo et al., "Appetite Suppression and Weight Loss after the Cannabinoid Antagonist SR 141716," Life Sciences, vol. 63, No. 8 pp. PL 113-117 (1998).
Alpermann, H.G. et al. "Pharmacological Effects of Hoe 249: A New Potential Antidepressant," Drug Development Research 25:267-282 (1992).
Kenji Tamura et al., "One-Pot Synthesis of Trifluoroacetimidoyl Halides", J. Org. Chem. 1993, 58, 32-38.
XP002335745, Apr. 9, 1991, Nippon Nohyaku Co. Ltd.
XP002335857, Oct. 19, 2001, D.M.T. Chan et al.
XP002335858, Jan. 10, 2003, G.A. Meier et al.
XP002335859, Apr. 22, 2001, W.L. Meyer et al.
International Search Report mailed Jul. 29, 2005 in International Application No. PCT/EP2005/001659.
Vippagunta, Sudha R. et al., "Crystalline Solids," (2001) Advanced Drug Delivery Reviews 48:3-26.
Vaughan, Wyman R., "2,3-Pyrrolidinediones, VI. Reactions with Phenyhydrazine," (1955), J. Org. Chem. 20(12):1619-1626.

* cited by examiner

SUBSTITUTED PYRAZOLINE COMPOUNDS, THEIR PREPARATION AND USE AS MEDICAMENTS

CROSS-REFERENCE TO RELATED APPLICATIONS

This application is a continuation-in-part of application Ser. No. 10/804,534, filed Mar. 19, 2004 now abandoned which claims priority to Spanish patent application No. 2004 00378 filed Feb. 17, 2004.

The present invention relates to substituted pyrazoline compounds, methods for their preparation, medicaments comprising these compounds as well as their use for the preparation of a medicament for the treatment of humans and animals.

Cannabinoids are compounds, which are derived from the cannabis sativa plant which is commonly known as marijuana. The most active chemical compound of the naturally occurring cannabinoids is tetrahydrocannabinol (THC), particularly $\Delta^9$-THC.

These naturally occurring cannabinoids as well as their synthetic analogues promote their physiological effects via binding to specific G-coupled receptors, the so-called cannabinoid-receptors.

At present, two distinct types of receptors that bind both the naturally occurring and synthetic cannabinoids have been identified and cloned. These receptors, which are designated $CB_1$ and $CB_2$ are involved in a variety of physiological or pathophysiological processes in humans and animals, e.g. processes related to the central nervous system, immune system, cardiovascular system, endocrinous system, respiratory system, the gastrointestinal tract or to reproduction, as described for example, in Hollister, Pharm. Rev. 38, 1986, 1-20; Reny and Singha, Prog. Drug. Res., 36, 71-114, 1991; Consroe and Sandyk, in Marijuana/Cannabinoids, Neurobiology and Neurophysiology, 459, Murphy L. and Barthe A. Eds., CRC Press, 1992.

Therefore, compounds, which have a high binding affinity for these cannabinoid receptors and which are suitable for modulating these receptors are useful in the prevention and/or treatment of cannabinoid-receptor related disorders.

In particular, the $CB_1$-Receptor is involved in many different food-intake related disorders such as bulimia or obesity, including obesity associated with type II diabetes (non-insulin-dependent diabetes) and thus, compounds suitable for regulating this receptor may be used in the prophylaxis and/or treatment of these disorders.

Thus, it was an object of the present invention to provide novel compounds for use as active substances in medicaments, which are suitable for the modulation of Cannabinoid receptors, particularly Cannabinoid 1 ($CB_1$) receptors.

Said object was achieved by providing the substituted pyrazoline compounds of general formula I given below, their stereoisomers, corresponding salts and corresponding solvates thereof.

It has been found that these compounds have a high affinity for cannabinoid receptors, particularly for the $CB_1$-receptor and that they act as antagonists on these receptors. They are therefore suitable for the prophylaxis and/or treatment of various disorders related to the central nervous system, the immune system, the cardiovascular system, the endocrinous system, the respiratory system, the gastrointestinal tract or reproduction in humans and/or animals, preferably humans including infants, children and grown-ups.

Thus, in one of its aspects the present invention relates to substituted pyrazoline compounds of general formula

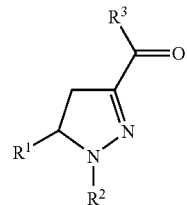

wherein $R^1$ represents an optionally at least mono-substituted phenyl group, $R^2$ represents an optionally at least mono-substituted phenyl group, $R^3$ represents a saturated or unsaturated, optionally at least mono-substituted, optionally at least one heteroatom as ring member containing cycloaliphatic group, which may be condensed with an optionally at least mono-substituted mono- or polycyclic ring system, or $R^3$ represents an optionally at least mono-substituted aryl or heteroaryl group, which may be condensed with an optionally at least mono-substituted mono- or polycyclic ring system, or $R^3$ represents an —NR$^4$R$^5$-moiety, $R^4$ and $R^5$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, an —SO$_2$—R$^6$-moiety, or an —NR$^7$R$^8$-moiety, $R^6$ represents a linear or branched, saturated or unsaturated, optionally at least mono-substituted aliphatic group, a saturated or unsaturated, optionally at least mono-substituted, optionally at least one heteroatom as ring member containing cycloaliphatic group, which may be condensed with a mono- or polycyclic ring-system, or an optionally at least mono-substituted aryl or heteroaryl group, which may be condensed with a mono- or polycyclic ring system and/or bonded via a linear or branched alkylene group, $R^7$ and $R^8$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Particularly preferably the following provisos (disclaimers) apply for the pyrazoline compounds of general formula I given above:

that $R^4$ and $R^5$ do not both represent a hydrogen atom, and that if one of the residues $R^4$ and $R^5$ represents a hydrogen atom or an alkyl group, which is optionally at least mono-substituted with an alkoxy group, an alkoxyalkoxy group, a halogen atom or a phenyl group, the other one of these residues $R^4$ and $R^5$ does not represent a pyrid-2-yl group, which is optionally mono-substituted in the 5-position, a pyrid-5-yl group, which is optionally mono-substituted in the 2-position, a pyrimid-5-yl group, which is optionally mono-substituted in the 2-position, a pyridaz-3-yl group, which is optionally mono-substituted in the 6-position, a pyrazin-5-yl group, which is optionally mono-substituted in the 2-position, a thien-2-yl group, which is optionally mono-substituted in the 5 position, a thien-2-yl group, which is optionally at least mono-substituted in the 4-position, a benzyl group, which is optionally mono-substituted in the 4-position of the ring, a phenethyl group, which is optionally mono-substituted in the 4-position of the ring, an optionally mono-, di- or tri-substituted phenyl group, a di-substituted phenyl group, wherein the two substituents together form an —OCH$_2$O—, —OCH$_2$CH$_2$O— or —CH$_2$CH$_2$O— chain, which is optionally substituted with one or more halogen atoms or one or two methyl groups, an —NH-phenyl-moiety, wherein the phenyl group may be mono-substituted in the 4-position, and that if one of the residues $R^4$ and $R^5$ represents an alkynyl group, the other one of these residues $R^4$ and $R^5$ does not represent a phenyl group, which is optionally substituted in the 4-position, and that if one of the residues $R^4$ and $R^5$ represents a hydrogen atom or a linear or branched, saturated or unsaturated, unsubstituted or substituted aliphatic radical, the other one of these residues $R^4$ and $R^5$ does not represent an unsubstituted or substituted thiazole group or an unsubstituted or substituted [1,3,4]thiadiazole group.

A mono- or polycyclic ring-system according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-system are preferably 5- or 6-membered. The term "condensed" according to the present invention means that a ring or ring-system is attached to another ring or ring-system, whereby the terms "annulated" or "annelated" are also used by those skilled in the art to designate this kind of attachment.

If one or more of the residues $R^3$—$R^8$ represents or comprises a saturated or unsaturated, optionally at least one heteroatom as ring member containing cycloaliphatic group, which is substituted by one or more substituents, unless defined otherwise, each of the substituents may be independently selected from the group consisting of hydroxy, fluorine, chlorine, bromine, branched or unbranched C$_{1-6}$-alkoxy, branched or unbranched C$_{1-6}$-alkyl, unbranched C$_{1-4}$-perfluoroalkoxy, branched or unbranched C$_{1-4}$-perfluoroalkyl, oxo, amino, carboxy, amido, cyano, nitro, —SO$_2$NH$_2$, —CO—C$_{1-4}$-alkyl, —SO—C$_{1-4}$-alkyl, —SO$_2$—C$_{1-4}$-alkyl, —NH—SO$_2$—C$_{1-4}$-alkyl, wherein the C$_{1-4}$-alkyl may in each case be branched or unbranched, and a phenyl group, more preferably be selected from the group consisting of hydroxy, F, Cl, Br, methyl, ethyl, methoxy, ethoxy, oxo, CF$_3$ and a phenyl group.

If one or more of the residues $R^3$—$R^8$ represents or comprises a cycloaliphatic group, which contains one or more heteroatoms as ring members, unless defined otherwise, each of these heteroatoms may preferably be selected from the group consisting of of N, O and S.

Suitable saturated or unsaturated, optionally at least one heteroatom as ring member containing, optionally at least mono-substituted cycloaliphatic groups may preferably be selected from the group consisting of Cyclopropyl, Cyclobutyl, Cyclopentyl, Cyclohexyl, Cycloheptyl, Cyclooctyl, Cyclopentenyl, Cyclohexenyl, Cycloheptenyl, Cyclooctenyl, Pyrrolidinyl, Piperidinyl, Piperazinyl, homo-Piperazinyl and Morpholinyl.

If one or more of the residues $R^3$—$R^8$ comprises a mono- or polycyclic ring system, which is substituted by one or more substituents, unless defined otherwise, each of the substituents may be independently selected from the group consisting of hydroxy, fluorine, chlorine, bromine, branched or unbranched C$_{1-6}$-alkoxy, branched or unbranched C$_{1-6}$-alkyl, branched or unbranched C$_{1-4}$-perfluoroalkoxy, branched or unbranched C$_{1-4}$-perfluoroalkyl, amino, carboxy, oxo, amido, cyano, nitro, —SO$_2$NH$_2$, —CO—C$_{1-4}$-alkyl, —SO—C$_{1-4}$alkyl, —SO$_2$—C$_{1-4}$-alkyl, —NH—SO$_2$—C$_{1-4}$-alkyl, wherein the C$_{1-4}$-alkyl may in each case be branched or unbranched, and a phenyl group, more preferably be selected from the group consisting of hydroxy, F, Cl, Br, methyl, ethyl, methoxy, ethoxy, CF$_3$, oxo and a phenyl group.

If one or more of the residues $R^1$—$R^8$ represents or comprises an aryl group, including a phenyl group, which is substituted by one or more substituents, unless defined otherwise, each of the substituents may be independently selected from the group consisting of a halogen atom, a linear or branched C$_{1-6}$-alkyl group, a linear or branched C$_{1-6}$ alcoxy group, a formyl group, a hydroxy group, a trifluoromethyl group, a trifluoromethoxy group, a —CO—C$_{1-6}$-alkyl group, a cyano group, a nitro group, a carboxy group, a —CO—O—C$_{1-6}$-alkyl group, a —CO—NR$^A$R$^B$-moiety, a —CO—NH—NR$^C$R$^D$— moiety, an —SH, an —S—C$_{1-6}$-alkyl group, an —SO—C$_{1-6}$-alkyl group, an —SO$_2$-C$_{1-6}$-alkyl group, a —C$_{1-6}$-alkylene-S—C$_{1-6}$-alkyl group, a —C$_{1-6}$-alkylene-SO—C$_{1-6}$-alkyl group, a —C$_{1-6}$-alkylene-SO$_2$—C$_{1-6}$-alkyl group, an —NH$_2$-moiety, an NHR'-moiety or an NR'R"-moiety, wherein R' and R" independently represent a linear or branched C$_{1-6}$-alkyl group, a C$_{1-6}$-alkyl group substituted by one or more hydroxy groups and a —C$_{1-6}$-alkylene-NR$^E$R$^F$ group, whereby $R^A$, $R^B$, identical or different, represent hydrogen or a C$_{1-6}$-alkyl group, or $R^A$ and $R^B$ together with the bridging nitrogen atom form a saturated, mono- or bicyclic, 3-10 membered heterocyclic ring system, which may be at least mono-substituted by one or more, identical or different, C$_{1-6}$ alkyl groups and/or which may contain at least one further heteroatom selected from the group consisting of nitrogen, oxygen and sulphur as a ring member, $R^C$, $R^D$, identical or different, represent a hydrogen atom, a C$_{1-6}$-alkyl group, a —CO—O—C$_{1-6}$-alkyl group, a C$_{3-8}$-cycloalkyl group, a C$_{1-8}$-alkylene-C$_{3-8}$-cycloalkyl group, C$_{1-6}$-alkylene-O—C$_{1-6}$-alkyl group or a C$_{1-6}$-alkyl group substituted with one or more hydroxy groups, or $R^C$, $R^D$ together with the bridging nitrogen atom form a saturated, mono- or bicyclic, 3-10 membered heterocyclic ring system, which may be at least mono-substituted by one or more substituents independently selected from the group consisting of C$_{1-6}$ alkyl group, a —CO—C$_{1-6}$-alkyl group, a —CO—O—C$_{1-6}$- alkyl group, a —CO—NH—$C_{1-6}$-alkyl group, a —CS—NH—$C_{1-6}$-alkyl group, an oxo group, a $C_{1-6}$-alkyl group substituted with one or more hydroxy groups, a $C_{1-6}$-alkylene-O—$C_{1-6}$-alkyl group and a —CO—NH$_2$ group and/or which may contain at least one further heteroatom selected from the group consisting of nitrogen, oxygen and sulphur as a ring member, and wherein $R^E$, $R^F$, identical or different, represent hydrogen or a $C_{1-6}$-alkyl group, or $R^E$ and $R^F$ together with the bridging nitrogen atom form a saturated, mono- or bicyclic, 3-10 membered heterocyclic ring system, which may be at least mono-substituted by one or more, identical or different $C_{1-6}$ alkyl groups and/or which may contain at least one further heteroatom selected from the group consisting of nitrogen, oxygen and sulphur as a ring member.

Preferred aryl groups, which may optionally be at least mono-substituted, are phenyl and naphthyl.

If one or more of the residues $R^3$—$R^8$ represents or comprises a heteroaryl group, which is substituted by one or more substituents, unless defined otherwise, each of the substituents may be independently selected from the group consisting of a halogen atom, a linear or branched $C_{1-6}$-alkyl group, a linear or branched $C_{1-6}$ alcoxy group, a formyl group, a hydroxy group, a trifluoromethyl group, a trifluoromethoxy group, a —CO—$C_{1-6}$-alkyl group, a cyano group, a carboxy group, a —CO—O—$C_{1-6}$-alkyl group, a —CO—NR$^A$R$^B$-moiety, a —CO—NH—NR$^C$R$^D$-moiety, an —S—$C_{1-6}$-alkyl group, an —SO—$C_{1-6}$-alkyl group, an —SO$_2$—$C_{1-6}$-alkyl group, a —$C_{1-6}$-alkylene-S—$C_{1-6}$-alkyl group, a —$C_{1-6}$-alkylene-SO—$C_{1-6}$-alkyl group, a —$C_{1-6}$-alkylene-SO$_2$-$C_{1-6}$ alkyl group, a $C_{1-6}$-alkyl group substituted by one or more hydroxy groups and a —$C_{1-6}$-alkylene-NR$^E$R$^F$ group, whereby $R^A$, $R^B$, identical or different, represent hydrogen or a $C_{1-6}$-alkyl group, or $R^A$ and $R^B$ together with the bridging nitrogen atom form a saturated, mono- or bicyclic, 3-10 membered heterocyclic ring system, which may be at least mono-substituted by one or more, identical or different, $C_{1-6}$ alkyl groups and/or which may contain at least one further heteroatom selected from the group consisting of nitrogen, oxygen and sulphur as a ring member, $R^C$, $R^D$, identical or different, represent a hydrogen atom, a $C_{1-6}$-alkyl group, a —CO—O—$C_{1-6}$-alkyl group, a $C_{3-8}$-cycloalkyl group, a $C_{1-6}$-alkylene-$C_{3-8}$-cycloalkyl group, $C_{1-6}$-alkylene-O—$C_{1-6}$-alkyl group or a $C_{1-6}$-alkyl group substituted with one or more hydroxy groups, or $R^C$, $R^D$ together with the bridging nitrogen atom form a saturated, mono- or bicyclic, 3-10 membered heterocyclic ring system, which may be at least mono-substituted by one or more substituents independently selected from the group consisting of $C_{1-6}$ alkyl group, a —CO—$C_{1-6}$-alkyl group, a —CO—O—$C_{1-6}$-alkyl group, a —CO—NH—$C_{1-6}$-alkyl group, a —CS—NH—$C_{1-6}$-alkyl group, an oxo group, a $C_{1-6}$-alkyl group substituted with one or more hydroxy groups, a $C_{1-6}$-alkylene-O—$C_{1-6}$-alkyl group and a —CO—NH$_2$ group and/or which may contain at least one further heteroatom selected from the group consisting of nitrogen, oxygen and sulphur as a ring member, and wherein $R^E$, $R^F$, identical or different, represent hydrogen or a $C_{1-6}$-alkyl group, or $R^E$ and $R^F$ together with the bridging nitrogen atom form a saturated, mono- or bicyclic, 3-10 membered heterocyclic ring system, which may be at least mono-substituted by one or more, identical or different $C_{1-6}$ alkyl groups and/or which may contain at least one further heteroatom selected from the group consisting of nitrogen, oxygen and sulphur as a ring member, The heteroatoms, which are present as ring members in the heteroaryl radical, may, unless defined otherwise, independently be selected from the group consisting of nitrogen, oxygen and sulphur.

Suitable heteroaryl groups, which may optionally be at least mono-substituted, may preferably be selected from the group consisting of thienyl, furyl, pyrrolyl, pyridinyl, imidazolyl, pyrimidinyl, pyrazinyl, indolyl, chinolinyl, isochinolinyl, benzo[1,2,5]-thiodiazolyl, benzo[b]thiophenyl, benzo[b]furanyl, imidazo[2,1-b]thiazolyl, triazolyl, and pyrazolyl, more preferably be selected from the group consisting of thienyl-, benzo[1,2,5]-thiodiazolyl, benzo[b]thiophenyl, imidazo[2,1-b]thiazolyl, triazolyl and pyrazolyl.

If one or more of the residues $R^4$—$R^8$ represents or comprises a linear or branched, saturated or unsaturated aliphatic group, which is substituted by one or more substituents, unless defined otherwise, each of the substituents may be independently selected from the group consisting of hydroxy, fluorine, chlorine, bromine, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, nitro, —SO$_2$NH$_2$, —CO—$C_{1-4}$-alkyl, —SO—$C_{1-4}$-alkyl, —SO$_2$—$C_{1-4}$-alkyl, —NH—SO$_2$—$C_{1-4}$-alkyl, wherein the $C_{1-4}$-alkyl may in each case be branched or unbranched, and a phenyl group, more preferably be selected from the group consisting of hydroxy, F, Cl, Br, methoxy, ethoxy, CF$_3$ and a phenyl group.

Preferred linear or branched, saturated or unsaturated aliphatic groups, which may be substituted by one or more substituents, may preferably be selected from the group consisting of methyl, ethyl, n-propyl, isopropyl, n-butyl, isobutyl, sec-butyl, tert-butyl, n-pentyl, n-hexyl, n-heptyl, noctyl, n-nonyl, n-decyl, vinyl, ethinyl, propenyl, propinyl, butenyl and butinyl.

If any of the residues $R^4$—$R^8$ represents or comprises a linear or branched alkylene group, said alkylene group may preferably be selected from the group consisting of -methylene-(CH$_2$)—, ethylene-(CH$_2$—CH$_2$)—, n-propylene-(CH$_2$—CH$_2$—CH$_2$)— or iso-propylene-(—C(CH$_3$)$_2$)—.

Preferred are substituted pyrazoline compounds of general formula I given above, wherein $R^1$ represents an optionally at least mono-substituted phenyl group, $R^2$ represents an optionally at least mono-substituted phenyl group, $R^3$ represents a saturated or unsaturated, optionally at least mono-substituted, optionally at least one heteroatom as ring member containing cycloaliphatic group, which may be condensed with an optionally at least mono-substituted mono- or polycyclic ring system, or $R^3$ represents an optionally at least mono-substituted aryl or heteroaryl group, which may be condensed with an optionally at least mono-substituted mono- or polycyclic ring system, or $R^3$ represents an —NR$^4$R$^5$-moiety, $R^4$ and $R^5$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, an —SO$_2$—R$^6$-moiety, or an —NR$^7$R$^8$-moiety, $R^6$ represents a linear or branched, saturated or unsaturated, optionally at least mono-substituted aliphatic group, a saturated or unsaturated, optionally at least mono-substituted, optionally at least one heteroatom as ring member containing cycloaliphatic group, which may be condensed with a mono- or polycyclic ring-system, or an optionally at least mono-substituted aryl or heteroaryl group, which may be condensed with a mono- or polycyclic ring system and/or bonded via a linear or branched alkylene group, $R^7$ and $R^8$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, whereby preferably the following provisos (disclaimers) apply:

that $R^4$ and $R^5$ do not both represent a hydrogen atom, and that if one of the residues $R^4$ and $R^5$ represents a hydrogen atom or a linear or branched, saturated or unsaturated; substituted or unsubstituted aliphatic group, the other one of these residues $R^4$ and $R^5$ does not represent a substituted or unsubstituted pyridyl group, a substituted or unsubstituted pyrimidyl group, a substituted or unsubstituted pyridazyl group, a substituted or unsubstituted pyrazinyl group, a substituted or unsubstituted thienyl group, a substituted or unsubstituted benzyl group, a substituted or unsubstituted phenethyl group, a substituted or unsubstituted phenyl group, a substituted or unsubstituted phenyl group, which is condensed (attached) to at least one, optionally substituted ring or ringsystem, an —NH-phenyl-moiety, wherein the phenyl group may be at least mono-substituted, an unsubstituted or substituted thiazole group, or an unsubstituted or substituted [1,3,4]thiadiazole group.

Preferred are also substituted pyrazoline compounds of general formula I given above, wherein $R^1$ represents a phenyl group, which is optionally substituted by one or more substituents independently selected from the group consisting of a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R", whereby R' and R" for each substituent independently represent linear or branched $C_{1-6}$ alkyl, preferably $R^1$ represents a phenyl group, which is optionally substituted by one or more substituents selected from the group consisting of methyl, ethyl, F, Cl, Br and $CF_3$, more preferably $R^1$ represents a phenyl group, which is substituted with a chlorine atom in the 4-position, and $R^2$—$R^8$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Also preferred are substituted pyrazoline compounds of general formula I given above, wherein $R^2$ represents a phenyl group, which is optionally substituted by one or more substituents independently selected from the group consisting of a linear or branched $C_{1-6}$-alkyl group, a linear or branched $C_{1-6}$-alkoxy group, a halogen atom, $CH_2F$, $CHF_2$, $CF_3$, CN, OH, $NO_2$, —(C=O)—R', SH, SR', SOR', $SO_2R'$, $NH_2$, NHR', NR'R", —(C=O)—$NH_2$, —(C=O)—NHR' and —(C=O)—NR'R" whereby R' and R" for each substituent independently represent linear or branched $C_{1-6}$ alkyl, preferably $R^2$ represents a phenyl group, which is optionally substituted by one or more substituents selected from the group consisting of methyl, ethyl, F, Cl, Br and $CF_3$, more preferably $R^2$ a phenyl group, which is di-substituted with two chlorine atoms in the 2- and 4-position, and $R^1$ and $R^3$—$R^8$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Preference is also given to substituted pyrazoline compounds of general formula I given above, wherein $R^3$ represents a saturated or unsaturated, optionally at least mono-substituted, optionally at least one heteroatom as ring member containing $C_{3-8}$ cycloaliphatic group, which may be condensed with an optionally at least mono-substituted mono- or polycyclic ring system, or $R^3$ represents an optionally at least mono-substituted, 5- or 6-membered aryl or heteroaryl group, which may be condensed with an optionally at least mono-substituted mono- or polycyclic ring system, or $R^3$ represents an —$NR^4R^5$-moiety, preferably $R^3$ represents a saturated, optionally at least mono-substituted, optionally one or more nitrogen-atoms as ring member containing $C_{3-8}$ cycloaliphatic group, which may be condensed with an optionally at least mono-substituted mono- or polycyclic ring system, or $R^3$ represents an —$NR^4R^5$-moiety, more preferably $R^3$ represents a pyrrolidinyl group, a piperidinyl group or a piperazinyl group, whereby each of these groups may be substituted with one or more $C_{1-6}$-alkyl groups, or $R^3$ represents an —$NR^4R^5$-moiety and $R^1$, $R^2$ and $R^4$—$R^8$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Furthermore, substituted pyrazoline compounds of general formula I given above are preferred, wherein $R^4$ and $R^5$, identical or different, represent a hydrogen atom, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system and/or bonded via a methylene (—$CH_2$—) or ethylene (—$CH_2$—$CH_2$)-group, an —$SO_2$—$R^6$-moiety, or an —$NR^7R^8$-moiety, preferably one of these residues $R^4$ and $R^5$ represents a hydrogen atom and the other one of these residues $R^4$ and $R^5$ represents a saturated or unsaturated, optionally at least mono-substituted, optionally at least one heteroatom as ring member containing $C_{3-8}$- cycloaliphatic group, which may be condensed with an optionally at least mono-substituted mono- or polycyclic ring system, or an optionally at least mono-substituted, 5- or 6-membered aryl or heteroaryl group, which may be condensed with an optionally at least mono-substituted mono- or polycyclic ring system, an —SO$_2$—R$^6$-moiety, or an —NR$^7$R$^8$-moiety, or R$^4$ and R$^5$, identical or different, each represent a C$_{1-6}$ alkyl group, more preferably one of these residues R$^4$ and R$^5$ represents a hydrogen atom and the other one of these residues R$^4$ and R$^5$ represents an optionally at least mono-substituted pyrrolidinyl group, an optionally at least mono-substituted piperidinyl group, an optionally at least mono-substituted piperazinyl group, an optionally at least mono-substituted triazolyl group, an —SO$_2$—R$^6$-moiety, or an —NR$^7$R$^8$-moiety, or R$^4$ and R$^5$, identical or different, represent a methyl group, an ethyl group, an n-propyl group, an isopropyl group, an n-butyl group, a sec-butyl group or a tert.-butyl group, and R$^1$—R$^3$ and R$^6$—R$^8$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Also preferred are substituted pyrazoline compounds of general formula I given above, wherein R$^6$ represents a linear or branched, saturated or unsaturated, optionally at least mono-substituted C$_{1-6}$ aliphatic group, a saturated or unsaturated, optionally at least mono-substituted, optionally at least one heteroatom as ring member containing C$_{3-8}$ cycloaliphatic group, which may be condensed with a mono- or polycyclic ring-system, or an optionally at least mono-substituted, 5- or 6-membered aryl or heteroaryl group, which may be condensed with a mono- or polycyclic ring system and/or bonded via a methylene (—CH$_2$—) or ethylene (—CH$_2$—CH$_2$)-group, preferably R$^6$ represents a C$_{1-6}$-alkyl group, a saturated, optionally at least mono-substituted cycloaliphatic group, which may be condensed with a mono- or polycyclic ring-system, or a phenyl group, which is optionally substituted with one or more C$_{1-6}$ alkyl groups, and R$^1$—R$^5$, R$^7$ and R$^8$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Moreover substituted pyrazoline compounds of general formula I given above are preferred, wherein R$^7$ and R$^8$, identical or different, represent a hydrogen atom, an unbranched or branched, saturated or unsaturated, optionally at least mono-substituted C$_{1-6}$ aliphatic radical, a saturated or unsaturated, optionally at least mono-substituted, optionally at least one heteroatom as ring member containing C$_{3-8}$ cycloaliphatic group, which may be condensed with an optionally at least mono-substituted mono- or polycyclic ring system, or an optionally at least mono-substituted, 5- or 6 membered aryl or heteroaryl group, which may be condensed with an optionally at least mono-substituted mono- or polycyclic ring system and/or bonded via a methylene (—CH$_2$—) or ethylene (—CH$_2$—CH$_2$)-group, preferably represent a hydrogen atom or a C$_{1-6}$ alkyl radical, and R$^1$—R$^6$ have the meaning given above, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Particularly preferred are compounds of general formula I given below,

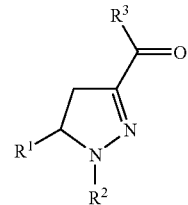

wherein

R$^1$ represents a phenyl ring, which is mono-substituted with a halogen atom, preferably a chlorine atom, in its 4-position, R$^2$ represents a phenyl ring, which is di-substituted with two halogen atoms, preferably chlorine atoms, in its 2- and 4-position, R$^3$ represents a pyrrolidinyl group, a piperidinyl group, a piperazinyl group, a homo-piperazinyl group, a morpholinyl group, or an —NR$^4$R$^5$-moiety, R$^4$ represents a hydrogen atom or a linear or branched C$_{1-6}$-alkyl group, R$^5$ represents a linear or branched C$_{1-6}$ alkyl group, a pyrrolidinyl group, a piperidinyl group, a piperazinyl group, a homo-piperazinyl group, a morpholinyl group, a triazolyl group, whereby each of the heterocyclic rings may be substituted with one or more, identical or different, C$_{1-6}$-alkyl groups, or an —SO$_2$—R$^6$-moiety, and R$^6$ represents a phenyl group, which is optionally substituted with one or more C$_{1-6}$ alkyl groups, which may be identical or different, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof.

Most particularly preferred are substituted pyrazoline compounds selected from the group consisting of:

N-piperidinyl-5-(4-chloro-phenyl)-1-(2,4-dichlorophenyl)-4,5-dihydro-1H-pyrazol-3-carboxamide, 5-(4-Chloro-phenyl)-1-(2,4-dichloro-phenyl)-4,5-dihydro-1H-pyrazole-3-carboxylic acid-[1,2,4]-triazole-4-yl-amide, 5-(4-Chloro-phenyl)-1-(2,4-dichlorophenyl)-4,5-dihydro-1H-pyrazole-3-carboxylic acid-(4-methyl-piperazin-1-yl)-amide, 5-(4-Chloro-phenyl)-1-(2,4-dichloro-phenyl)-4,5-dihydro-1H-pyrazole-3-carboxylic acid diethylamide,

[5-(4-Chloro-phenyl)-1-(2,4-dichloro-phenyl)-4,5-dihydro-1H-pyrazole-3-yl]-piperidine-1-yl-methanone, N-[5-(4-Chloro-phenyl)-1-(2,4-dichlorophenyl)-4,5-dihydro-1H-pyrazole-3-carbonyl]-4-methylphenylsufonamide, optionally in the form of a corresponding N-oxide, or a corresponding sad, or a corresponding solvate.

In another aspect the present invention also provides a process for the preparation of substituted pyrazoline com pounds of general formula given above, according to which at least one benzaldehyde compound of general formula II

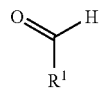 (II)

wherein $R^1$ has the meaning given above, is reacted with a pyruvate compound of general formula (III)

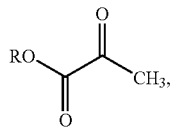 (III)

wherein R is a branched or unbranched $C_{1-6}$ alkyl radical, to yield a compound of general formula (IV)

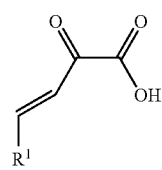 (IV)

wherein $R^1$ has the meaning given above, which is optionally isolated and/or optionally purified, and which is reacted with an optionally substituted phenyl hydrazine of general formula (V)

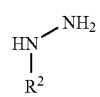 (V)

or a corresponding salt thereof, wherein $R^2$ has the meaning given above, under an inert atmosphere, to yield a compound of general formula (VI)

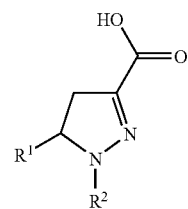 (VI)

wherein $R^1$ and $R^2$ have the meaning as given above, which is optionally isolated and/or optionally purified, and optionally transferred under inert atmosphere to a compound of general formula (VII)

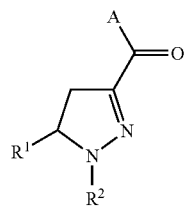 (VII)

wherein the substituents $R^1$ and $R^2$ have the meaning given above and A represents a leaving group, via the reaction with an activating agent, said compound being optionally isolated and/or optionally purified, and at least one compound of general formula (VI) is reacted with a compound of general formula $R^3H$, wherein $R^3$ represents an —$NR^4R^5$-moiety, wherein $R^4$ and $R^5$ have the meaning given above, to yield a substituted pyrazoline compound of general formula I, wherein $R^3$ represents an —$NR^4R^5$-moiety, and/or at least one compound of general formula (VII) is reacted with a compound of the general formula $R^3H$, in which $R^3$ has the meaning given above to yield a compound of general formula (I) given above, which is optionally isolated and/or optionally purified.

The inventive process is also illustrated in scheme I given below:

Scheme I

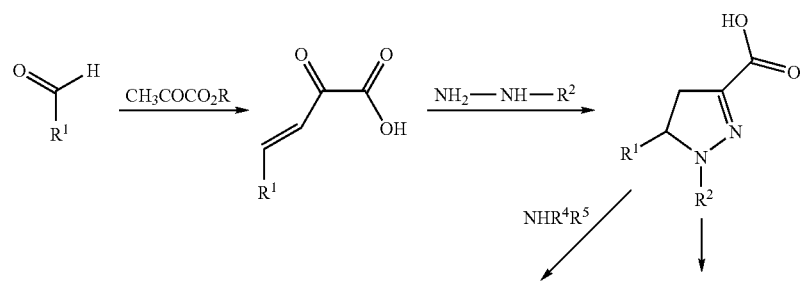

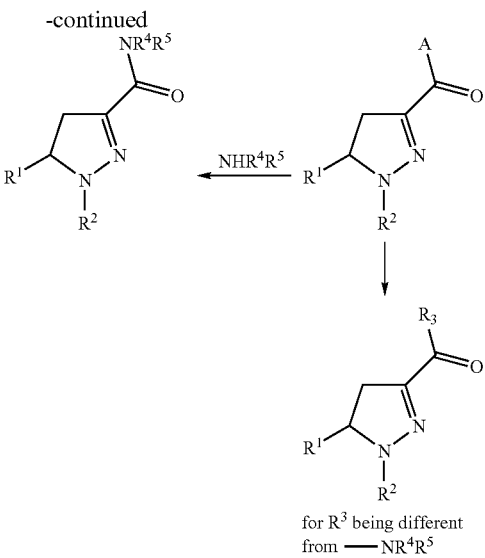

for R³ being different from —NR⁴R⁵

The reaction of the benzaldehyde compound of general formula II with a pyruvate compound of general formula III is preferably carried out in the presence of at least one base, more preferably in the presence of an alkali metal hydroxide such as sodium hydroxide or potassium hydroxide or an alkali metal methoxide such as sodium methoxide, as described, for example, in Synthetic communications, 26(11), 2229-33, (1996). The respective description is hereby incorporated by reference and forms part of the disclosure. Preferably said reaction is carried out in a protic reaction medium such as a $C_{1-4}$ alkyl alcohol or mixtures of these.

Reaction temperature as well as the duration of the reaction may vary over a broad range. Preferred reaction temperatures range from −10° C. to the boiling point of the reaction medium. Suitable reaction times may vary for example from several minutes to several hours.

Also preferred the reaction of the benzaldehyde compound of general formula II with a pyruvate compound of general formula III is carried out under acid catalysed conditions, more preferably by refluxing the mixture in dichloromethane in the presence of copper(II)trifluoromethanesulfonate as described, for example, in Synlett, (1), 147-149, 2001. The respective description is hereby incorporated by reference and forms part of the disclosure.

The reaction of the compound of general formula (IV) with an optionally substituted phenyl hydrazin of general formula (V) is preferably carried out in a suitable reaction medium such as $C_{1-4}$-alcohols or ethers such as dioxane or tetrahydrofurane or mixtures of at least two of these afore mentioned compounds. Also preferably, said reaction may be carried out in the presence of an acid, whereby the acid may be organic such as acetic acid and/or inorganic such as hydrochloric acid. Furthermore, the reaction may also be carried out in the presence of a base such as piperidine, piperazine, sodium hydroxide, potassium hydroxide, sodium methoxide or sodium ethoxide, or a mixture of at least two of these bases may also be used.

Reaction temperature as well as the duration of the reaction may vary over a broad range. Suitable reaction temperatures range from room temperature, i.e. approximately 25° C. to the boiling point of the reaction medium. Suitable reaction times may vary for example from several minutes to several hours.

The carboxylic group of the compound of general formula (VI) may be activated for further reactions by the introduction of a suitable leaving group according to conventional methods well known to those skilled in the art. Preferably the compounds of general formula (VI) are transferred into an acid chloride, an acid anhydride, a mixed anhydride, a $C_{1-4}$ alkyl ester, an activated ester such as p-nitrophenylester. Other well known methods for the activation of acids include the activation with N,N-dicyclohexylcarbodiimide or benzotriazol-N-oxotris(dimethylamino) phosphonium hexafluorophosphate (BOP)).

If said activated compound of general formula (VII) is an acid chloride, it is preferably prepared by reaction of the corresponding acid of general formula (VI) with thionyl chloride or oxalyl chloride, whereby said chlorinating agent is also used as the solvent. Also preferably an additional solvent may be used. Suitable solvents include hydrocarbons such as benzene, toluene or xylene, halogenated hydrocarbons such as dichloromethane, chloroform or carbon tetrachloride, ethers such as diethyl ether, dioxane, tetrahydrofurane or dimethoxyethane. Mixtures of two or more solvents from one class or two or more solvents from different classes may also be used. Preferred reaction temperature range from 0° C. to the boiling point of the solvent and reaction times from several minutes to several hours.

If said activated compound of general formula (VII) is a mixed anhydride, said anhydride may preferably be prepared, for example, by reaction of the corresponding acid of general formula (VI) with ethyl chloroformiate in the presence of a base such as triethylamine or pyridine, in a suitable solvent.

The reaction of general formula (VII) with a compound of general formula HR³ to yield compounds of general general I, wherein R³ represents an —NR⁴R⁵ moiety is preferably carried out in presence of a base such as triethylamine in a reaction medium such as methylenchloride. The temperature is preferably in the range from 0° C. to the boiling point of the reaction medium. The reaction time may vary over a broad range, e.g. from several hours to several days.

The reaction of general formula (VII) with a compound of general formula HR³ to yield compounds of general formula I, wherein R³ represents a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system may be carried out according to conventional methods well known to those skilled in the art, e.g. from Pascual, A., J. Prakt Chem., 1999, 341(7), 695-700; Lin, S. et al., Heterocycles, 2001, 55(2), 265-277; Rao, P. et al., J. Org. Chem., 2000, 65(22), 7323-7344, Pearson D. E and Buehler, C. A., Synthesis, 1972, 533-542 and references cited therein. The respective descriptions are hereby incorporated by reference and form part of the present disclosure.

Preferably said reaction is carried out in the presence of a Lewis acid, which is preferably selected from the group consisting of $FeCl_3$, $ZnCl_2$ and $AlCl_3$, in a suitable reaction medium such as toluene, benzene, tetrahydrofurane or similar. The temperature is preferably in the range from 0° C. to the boiling point of the reaction medium, more preferably from 15 to 25° C. The reaction time may vary over a broad range, e.g. from several minutes to several hours.

The afore mentioned reactions involving the synthesis of the 4,5-dihydro-pyrazole ring or the reaction of a compound comprising said ring are carried out under an inert atmosphere, preferably nitrogen or argon, to avoid oxidation of the ring-system.

During the processes described above the protection of sensitive groups or of reagents may be necessary and/or desirable. The introduction of conventional protective groups as well as their removal may be performed by methods well-known to those skilled in the art.

If the substituted pyrazoline compounds of general formula (I) themselves are obtained in form of a mixture of stereoisomers, particularly enantiomers or diastereomers, said mixtures may be separated by standard procedures known to those skilled in the art, e.g. chromatographic methods or fractionalized crystallization with chiral reagents. It is also possible to obtain pure stereoisomers via stereoselective synthesis.

In a further aspect the present invention also provides a process for the preparation of salts of substituted pyrazoline compounds of general formula (I) and stereoisomers thereof, wherein at least one compound of general formula (I) having at least one basic group is reacted with at least one inorganic and/or organic acid, preferably in the presence of a suitable reaction medium. Suitable reaction media include, for example, any of the ones given above. Suitable inorganic acids include hydrochloric acid, hydrobromic acid, phosphoric acid, sulfuric acid, nitric acid, suitable organic acids are e.g. citric acid, maleic acid, fumaric acid, tartaric acid, or derivatives thereof, p-toluenesulfonic acid, methanesulfonic acid or camphersulfonic acid.

In yet a further aspect the present invention also provides a process for the preparation of salts of substituted pyrazoline compounds of general formula (I) or stereoisomers thereof, wherein at least one compound of general formula (I) having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical. Suitable reaction media are, for example, any of the ones given above.

Solvates, preferably hydrates, of the substituted pyrazoline compounds of general formula (I), of corresponding stereoisomers, of corresponding N-oxides or of corresponding salts thereof may also be obtained by standard procedures known to those skilled in the art.

Substituted pyrazoline compounds of general formula I, which comprise nitrogen-atom containing saturated, unsaturated or aromatic rings may also be obtained in the form of their N-oxides by methods well known to those skilled in the art.

The purification and isolation of the inventive substituted pyrazoline compounds of general formula (I), of a corresponding stereoisomer, or salt, or solvate or any intermediate thereof may, if required, be carried out by conventional methods known to those skilled in the art, e.g. chromatographic methods or recrystallization.

The substituted pyrazoline compounds of general formula (I) given below, their stereoisomers, corresponding N-oxides, corresponding salts thereof and corresponding solvates are toxicologically acceptable and are therefore suitable as pharmaceutical active substances for the preparation of medicaments.

It has been found that the substituted pyrazoline compounds of general formula I given below, stereoisomers thereof, N-oxides thereof, corresponding salts and corresponding solvates have a high affinity to cannabinoid receptors, particularly cannabinoid 1 ($CB_1$)-receptors, i.e. they act as antagonists on these receptors. In particular these pyrazoline compounds show little or no development of tolerance during treatment particularly with respect to food intake. After ending the treatment with the pyrazoline compounds, reduced increase of body weight is found compared to the pre-treatment level.

Thus, an other aspect of the present invention relates to a medicament comprising at least one substituted pyrazoline compound of general formula I,

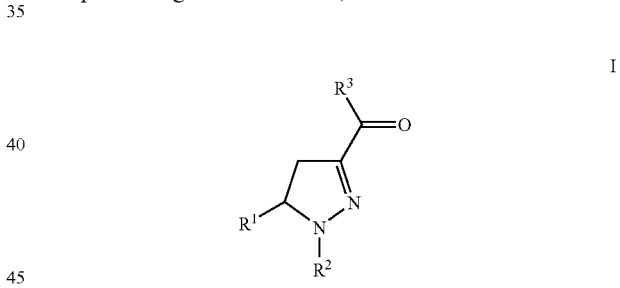

I wherein $R^1$ represents an optionally at least mono-substituted phenyl group, $R^2$ represents an optionally at least mono-substituted phenyl group, $R^3$ represents a saturated or unsaturated, optionally at least mono-substituted, optionally at least one heteroatom as ring member containing cycloaliphatic group, which may be condensed with an optionally at least mono-substituted mono- or polycyclic ring system, or $R^3$ represents an optionally at least mono-substituted aryl or heteroaryl group, which may be condensed with an optionally at least mono-substituted mono- or polycyclic ring system, or $R^3$ represents an —$NR^4R^5$-moiety, $R^4$ and $R^5$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, an —$SO_2$—$R^6$-moiety, or an —$NR^7R^8$-moiety, with the proviso that $R^4$ and $R^5$ do not identically represent hydrogen, $R^6$ represents a linear or branched, saturated or unsaturated, optionally at least mono-substituted aliphatic group, a saturated or unsaturated, optionally at least mono-substituted, optionally at least one heteroatom as ring member containing cycloaliphatic group, which may be condensed with a mono- or polycyclic ring-system, or an optionally at least mono-substituted aryl or heteroaryl group, which may be condensed with a mono- or polycyclic ring system and/or bonded via a linear or branched alkylene group, $R^7$ and $R^8$, identical or different, represent a hydrogen atom, an unbranched or branched, saturated or unsaturated, optionally at least mono-substituted aliphatic radical, a saturated or unsaturated, optionally at least mono-substituted, optionally at least one heteroatom as ring member containing cycloaliphatic group, which may be condensed with an optionally at least mono-substituted mono- or polycyclic ring system, or an optionally at least mono-substituted aryl or heteroaryl group, which may be condensed with an optionally at least mono-substituted mono- or polycyclic ring system and/or bonded via a linear or branched alkylene group, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients.

A mono- or polycyclic ring-system according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-system are preferably 5- or 6-membered. The term "condensed" according to the present invention means that a ring or ring-system is attached to another ring or ring-system, whereby the terms "annulated" or "annelated" are also used by those skilled in the art to designate this kind of attachment.

If one or more of the residues $R^3$—$R^8$ represents or comprises a saturated or unsaturated, optionally at least one heteroatom as ring member containing cycloaliphatic group, which is substituted by one or more substituents, unless defined otherwise, each of the substituents may be independently selected from the group consisting of hydroxy, fluorine, chlorine, bromine, branched or unbranched $C_{1-6}$-alkoxy, branched or unbranched $C_{1-6}$-alkyl, unbranched $C_{1-4}$-perfluoroalkoxy, branched or unbranched $C_{1-4}$-perfluoroalkyl, oxo, amino, carboxy, amido, cyano, nitro, —$SO_2NH_2$, —$CO$—$C_{1-4}$-alkyl, —$SO$—$C_{1-4}$-alkyl, —$SO_2C_{1-4}$-alkyl, —$NH$—$S_2C_{1-4}$-alkyl, wherein the $C_{1-4}$-alkyl may in each case be branched or unbranched, and a phenyl group, more preferably be selected from the group consisting of hydroxy, F, Cl, Br, methyl, ethyl, methoxy, ethoxy, oxo, $CF_3$ and a phenyl group.

If one or more of the residues $R^3$—$R^8$ represents or comprises a cycloaliphatic group, which contains one or more heteroatoms as ring members, unless defined otherwise, each of these heteroatoms may preferably be selected from the group consisting of of N, O and S.

Suitable saturated or unsaturated, optionally at least one heteroatom as ring member containing, optionally at least mono-substituted cycloaliphatic groups may preferably be selected from the group consisting of Cyclopropyl, Cyclobutyl, Cyclopentyl, Cyclohexyl, Cycloheptyl, Cyclooctyl, Cyclopentenyl, Cyclohexenyl, Cycloheptenyl, Cyclooctenyl, Pyrrolidinyl, Piperidinyl, Piperazinyl, homo-Piperazinyl and Morpholinyl.

If one or more of the residues $R^3$—$R^8$ comprises a mono- or polycyclic ring system, which is substituted by one or more substituents, unless defined otherwise, each of the substituents may be independently selected from the group consisting of hydroxy, fluorine, chlorine, bromine, branched or unbranched $C_{1-6}$-alkoxy, branched or unbranched $C_{1-6}$-alkyl, branched or unbranched $C_{1-4}$-perfluoroalkoxy, branched or unbranched $C_{1-4}$-perfluoroalkyl, amino, carboxy, oxo, amido, cyano, nitro, —$SO_2NH_2$, —$CO$—$C_{1-4}$-alkyl, —$SO$—$C_{1-4}$-alkyl, —$SO_2$—$C_{1-4}$-alkyl, —$NH$—$SO_2$—$C_{1-4}$-alkyl, wherein the $C_{1-4}$-alkyl may in each case be branched or unbranched, and a phenyl group, more preferably be selected from the group consisting of hydroxy, F, Cl, Br, methyl, ethyl, methoxy, ethoxy, $CF_3$, oxo and a phenyl group.

If one or more of the residues $R^1$—$R^8$ represents or comprises an aryl group, including a phenyl group, which is substituted by one or more substituents, unless defined otherwise, each of the substituents may be independently selected from the group consisting of a halogen atom, a linear or branched $C_{1-6}$-alkyl group, a linear or branched $C_{1-6}$ alcoxy group, a formyl group, a hydroxy group, a trifluoromethyl group, a trifluoromethoxy group, a —$CO$—$C_{1-6}$-alkyl group, a cyano group, a nitro group, a carboxy group, a —$CO$—$O$—$C_{1-6}$-alkyl group, a —$CO$—$NR^AR^B$-moiety, a —$CO$—$NH$—$NR^CR^D$-moiety, an —$SH$, an —$S$—$C_{1-6}$-alkyl group, an —$SO$—$C_{1-6}$-alkyl group, an —$SO_2$—$C_{1-6}$-alkyl group, a —$C_{1-6}$-alkylene-S—$C_{1-6}$-alkyl group, a —$C_{1-6}$-alkylene-SO—$C_{1-6}$-alkyl group, a —$C_{1-6}$-alkylene-$SO_2$—$C_{1-6}$-alkyl group, an —$NH_2$-moiety, an NHR'-moiety or an NR'R"-moiety, wherein R' and R" independently represent a linear or branched $C_{1-6}$-alkyl group, a $C_{1-6}$-alkyl group substituted by one or more hydroxy groups and a —$C_{1-6}$-alkylene-$NR^ER^F$ group, whereby $R^A$, $R^B$, identical or different, represent hydrogen or a $C_{1-6}$-alkyl group, or $R^A$ and $R^B$ together with the bridging nitrogen atom form a saturated, mono- or bicyclic, 3-10 membered heterocyclic ring system, which may be at least mono-substituted by one or more, identical or different, $C_{1-6}$ alkyl groups and/or which may contain at least one further heteroatom selected from the group consisting of nitrogen, oxygen and sulphur as a ring member, $R^C$, $R^D$, identical or different, represent a hydrogen atom, a $C_{1-6}$-alkyl group, a —$CO$—$O$—$C_{1-6}$-alkyl group, a $C_{3-8}$-cycloalkyl group, a $C_{1-6}$-alkylene-$C_{3-8}$-cycloalkyl group, $C_{1-6}$-alkylene-O—$C_{1-6}$-alkyl group or a $C_{1-6}$-alkyl group substituted with one or more hydroxy groups, or $R^C$, $R^D$ together with the bridging nitrogen atom form a saturated, mono- or bicyclic, 3-10 membered heterocyclic ring system, which may be at least mono-substituted by one or more substituents independently selected from the group consisting of $C_{1-6}$ alkyl group, a —$CO$—$C_{1-6}$-alkyl group, a —$CO$—$O$—$C_{1-6}$- alkyl group, a —CO—NH—$C_{1-6}$-alkyl group, a —CS—NH—$C_{1-6}$-alkyl group, an oxo group, a $C_{1-6}$-alkyl group substituted with one or more hydroxy groups, a $C_{1-6}$-alkylene-O—$C_{1-6}$-alkyl group and a —CO—$NH_2$ group and/or which may contain at least one further heteroatom selected from the group consisting of nitrogen, oxygen and sulphur as a ring member, and wherein $R^E$, $R^F$, identical or different, represent hydrogen or a $C_{1-6}$-alkyl group, or $R^E$ and $R^F$ together with the bridging nitrogen atom form a saturated, mono- or bicyclic, 3-10 membered heterocyclic ring system, which may be at least mono-substituted by one or more, identical or different $C_{1-6}$ alkyl groups and/or which may contain at least one further heteroatom selected from the group consisting of nitrogen, oxygen and sulphur as a ring member.

Preferred aryl groups, which may optionally be at least mono-substituted, are phenyl and naphthyl.

If one or more of the residues $R^3$—$R^8$ represents or comprises a heteroaryl group, which is substituted by one or more substituents, unless defined otherwise, each of the substituents may be independently selected from the group consisting of a halogen atom, a linear or branched $C_{1-6}$-alkyl group, a linear or branched $C_{1-6}$ alcoxy group, a formyl group, a hydroxy group, a trifluoromethyl group, a trifluoromethoxy group, a —CO—$C_{1-6}$-alkyl group, a cyano group, a carboxy group, a —CO—O—$C_{1-6}$-alkyl group, a —CO—$NR^AR^B$-moiety, a —CO—NH—$NR^CR^D$-moiety, an —S—$C_{1-6}$-alkyl group, an —SO—$C_{1-6}$-alkyl group, an —$SO_2$—$C_{1-6}$-alkyl group, a —$C_{1-6}$-alkylene-S—$C_{1-6}$-alkyl group, a —$C_{1-6}$-alkylene-SO—$C_{1-6}$-alkyl group, a —$C_{1-6}$-alkylene-$SO_2$—$C_{1-6}$-alkyl group, a $C_{1-6}$-alkyl group substituted by one or more hydroxy groups and a —$C_{1-6}$-alkylene-$NR^ER^F$ group, whereby $R^A$, $R^B$, identical or different, represent hydrogen or a $C_{1-6}$-alkyl group, or $R^A$ and $R^B$ together with the bridging nitrogen atom form a saturated, mono- or bicyclic, 3-10 membered heterocyclic ring system, which may be at least mono-substituted by one or more, identical or different, $C_{1-6}$ alkyl groups and/or which may contain at least one further heteroatom selected from the group consisting of nitrogen, oxygen and sulphur as a ring member, $R^C$, $R^D$, identical or different, represent a hydrogen atom, a $C_{1-6}$-alkyl group, a —CO—O—$C_{1-6}$-alkyl group, a $C_{3-8}$-cycloalkyl group, a $C_{1-6}$-alkylene-$C_{3-8}$-cycloalkyl group, $C_{1-6}$-alkylene-O—$C_{1-6}$-alkyl group or a $C_{1-6}$-alkyl group substituted with one or more hydroxy groups, or $R^C$, $R^D$ together with the bridging nitrogen atom form a saturated, mono- or bicyclic, 3-10 membered heterocyclic ring system, which may be at least mono-substituted by one or more substituents independently selected from the group consisting of $C_{1-6}$ alkyl group, a —CO—$C_{1-6}$-alkyl group, a —CO—O—$C_{1-6}$-alkyl group, a —CO—NH—$C_{1-6}$-alkyl group, a —CS—NH—$C_{1-6}$-alkyl group, an oxo group, a $C_{1-6}$-alkyl group substituted with one or more hydroxy groups, a $C_{1-6}$-alkylene-O—$C_{1-6}$-alkyl group and a —CO—$NH_2$ group and/or which may contain at least one further heteroatom selected from the group consisting of nitrogen, oxygen and sulphur as a ring member, and wherein $R^E$, $R^F$, identical or different, represent hydrogen or a $C_{1-6}$-alkyl group, or $R^E$ and $R^F$ together with the bridging nitrogen atom form a saturated, mono- or bicyclic, 3-10 membered heterocyclic ring system, which may be at least mono-substituted by one or more, identical or different $C_{1-6}$ alkyl groups and/or which may contain at least one further heteroatom selected from the group consisting of nitrogen, oxygen and sulphur as a ring member, The heteroatoms, which are present as ring members in the heteroaryl radical, may, unless defined otherwise, independently be selected from the group consisting of nitrogen, oxygen and sulphur.

Suitable heteroaryl groups, which may optionally be at least mono-substituted, may preferably be selected from the group consisting of thienyl, furyl, pyrrolyl, pyridinyl, imidazolyl, pyrimidinyl, pyrazinyl, indolyl, chinolinyl, isochinolinyl, benzo[1,2,5]-thiodiazolyl, benzo[b]thiophenyl, benzo[b]furanyl, imidazo[2,1-b]thiazolyl, triazolyl, and pyrazolyl, more preferably be selected from the group consisting of thienyl-, benzo[1,2,5]-thiodiazolyl, benzo[b]thiophenyl, imidazo[2,1-b]thiazolyl, triazolyl and pyrazolyl.

If one or more of the residues $R^4$—$R^8$ represents or comprises a linear or branched, saturated or unsaturated aliphatic group, which is substituted by one or more substituents, unless defined otherwise, each of the substituents may be independently selected from the group consisting of hydroxy, fluorine, chlorine, bromine, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein the $C_{1-4}$-alkyl may in each case be branched or unbranched, and a phenyl group, more preferably be selected from the group consisting of hydroxy, F, Cl, Br, methoxy, ethoxy, $CF_3$ and a phenyl group.

Preferred linear or branched, saturated or unsaturated aliphatic groups, which may be substituted by one or more substituents, may preferably be selected from the group consisting of methyl, ethyl, n-propyl, isopropyl, n-butyl, isobutyl, sec-butyl, tert-butyl, n-pentyl, n-hexyl, n-heptyl, n-octyl, n-nonyl, n-decyl, vinyl, ethinyl, propenyl, propinyl, butenyl and butinyl.

If any of the residues $R^4$—$R^8$ represents or comprises a linear or branched alkylene group, said alkylene group may preferably be selected from the group consisting of -methylene-($CH_2$)—, ethylene-($CH_2$—$CH_2$)—, n-propylene-($CH_2$—$CH_2CH_2$)— or iso-proylene-(—$C(CH_3)_2$)—.

The inventive medicament may preferably also comprise any of the inventive pyrazoline compounds or combinations of at least two of these pyrazoline compounds given above.

Said medicament may also comprise any combination of one or more of the substituted pyrazoline compounds of general formula I given above, stereoisomers thereof, corresponding N-oxides thereof, physiologically acceptable salts thereof or physiologically acceptable solvates thereof.

Preferably said medicament is suitable for the modulation (regulation) of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferably said medicament is suitable for the prophylaxis and/or treatment of psychosis.

Also particularly preferably said medicament is suitable for the prophylaxis and/or treatment of food intake disorders, preferably bulimia, anorexia, cachexia, obesity and/or type II diabetus mellitus (non-insuline dependent diabetes mellitus), preferably obesity.

Particularly preferably said medicament is suitable for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction.

Medicaments and/or drugs, which are frequently the subject of misuse include opioids, barbiturates, cannabis, cocaine, amphetamines, phencyclidine, hallucinogens and benzodiazepines.

The medicament is also suitable for the prophylaxis and/or treatment of one or more disorders selected from the group consisting of schizophrenia, anxiety, depression, epilepsy, neurodegenerative disorders, cerebellar disorders, spinocerebellar disorders, cognitive disorders, cranial trauma, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, cancer, medicament-induced movement disorders, dystonia, endotoxemic shock, hemorragic shock, hypotension, insomnia, immunologic disorders, sclerotic plaques, vomiting, diarrhea, asthma, memory disorders, pruritus, pain, or for potentiation of the analgesic effect of narcotic and non-narcotic analgesics, or for influencing intestinal transit.

Another aspect of the present invention is the use of at least one substituted pyrazoline compound of general formula I given above as suitable active substances for the medicament, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the modulation of cannabinoid-receptors, preferably cannabinoid 1 ($CB_1$) receptors, for the prophylaxis and/or treatment of disorders of the central nervous system, disorders of the immune system, disorders of the cardiovascular system, disorders of the endocrinous system, disorders of the respiratory system, disorders of the gastrointestinal tract or reproductive disorders.

Particularly preferred is the use of at least one of the respective pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of psychosis.

Also particularly preferred is the use of at least one of the respective pyrazoline compounds, optionally in form of one of the stereoisomers, preferably enantiomers or diastereomers, a racemate or in form of a mixture of at least two of the stereoisomers, preferably enanbomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of food intake disorders, preferably bulimia, anorexia, cachexia, obesity and/or type II diabetus mellitus (non-insuline dependent diabetes mellitus), preferably obesity.

Also particularly preferred is the use of at least one of the respective pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of alcohol abuse and/or alcohol addiction, nicotine abuse and/or nicotine addiction, drug abuse and/or drug addiction and/or medicament abuse and/or medicament addiction, preferably drug abuse and/or drug addiction.

Medicaments/drugs, which are frequently the subject of misuse include opioids, barbiturates, cannabis, cocaine, amphetamines, phencyclidine, hallucinogens and benzodiazepines.

Also preferred is the use of at least one of the respective pyrazoline compounds, optionally in form of one of the stereoisomers, preferably enantiomers or diastereomers, a racemate or in form of a mixture of at least two of the stereoisomers, preferably enantiomers and/or diastereomers, in any mixing ratio, or a corresponding N-oxide thereof, or a corresponding salt thereof, or a corresponding solvate thereof, and optionally one or more pharmaceutically acceptable excipients, for the preparation of a medicament for the prophylaxis and/or treatment of one or more disorders selected from the group consisting of schizophrenia, anxiety, depression, epilepsy, neurodegenerative disorders, cerebellar disorders, spinocerebellar disorders, cognitive disorders, cranial trauma, panic attacks, peripheric neuropathy, inflammation, glaucoma, migraine, Morbus Parkinson, Morbus Huntington, Morbus Alzheimer, Raynaud's disease, tremblement disorders, compulsive disorders, senile dementia, thymic disorders, tardive dyskinesia, bipolar disorders, cancer, medicament-induced movement disorders, dystonia, endotoxemic shock, hemorragic shock, hypotension, insomnia, immunologic disorders, sclerotic plaques, vomiting, diarrhea, asthma, memory disorders, pruritus, pain, or for potentiation of the analgesic effect of narcotic and non-narcotic analgesics, or for influencing intestinal transit.

The medicament according to the present invention may be in any form suitable for the application to humans and/or animals, preferably humans including infants, children and adults and can be produced by standard procedures known to those skilled in the art. The composition of the medicament may vary depending on the route of administration, The medicament of the present invention may for example be administered parentally in combination with conventional injectable liquid carriers, such as water or suitable alcohols. Conventional pharmaceutical excipients for injection, such as stabilizing agents, solubilizing agents, and buffers, may be included in such injectable compositions. These medicaments may for example be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, aqueous or oily solutions, suspensions, emulsions, or dry powdered forms suitable for reconstitution with water or other suitable liquid medium before use, for immediate or retarded release.

The liquid oral forms for administration may also contain certain additives such as sweeteners, flavoring, preservatives, and emulsifying agents. Non-aqueous liquid compositions for oral administration may also be formulated, containing edible oils. Such liquid compositions may be conveniently encapsulated in e.g., gelatin capsules in a unit dosage amount.

The compositions of the present invention may also be administered topically or via a suppository.

The daily dosage for humans and animals may vary depending on factors that have their basis in the respective species or other factors, such as age, sex, weight or degree of illness and so forth. The daily dosage for humans may preferably be in the range from 1 to 2000, preferably 1 to 1500, more preferably 1 to 1000 milligrams of active substance to be administered during one or several intakes per day.

Pharmacological Methods

I. In-vitro Determination of Affinity to CB1/CB2-Receptors

The in-vitro determination of the affinity of the inventive substituted pyrazoline compounds to $CB_1/CB_2$-Rezeptors is carried out as described in the publication of Ruth A. Ross, Heather C. Brockie et al., "Agonist-inverse agonist characterization at $CB_1$ and $CB_2$ cannabinoid receptors of L-759633, L759656 and AM630", British Journal of Pharmacology, 126, 665-672, (1999), whereby the transfected human $CB_1$ and $CB_2$ receptors of Receptor Biology, Inc. are used. The radioligand used for both receptors is [$^3$H]-CP55940. The respective parts of the description is hereby incorporated by reference and forms part of the present disclosure.

II. In-vivo Bioassay System for Determination of Cannabinoid Activity

Mouse Tetrad Model

Substances with affinity for cannabinoid receptors are known to produce a wide range of pharmacological effects. It is also known that intravenous administration of a substance with affinity for cannabinoid receptors in mice produces analgesia, hypothermia, sedation and catalepsy. Individually, none of these effects can be considered as proof that a tested substance has affinity for cannabinoid-receptors, since all of these effects are common for various classes of centrally active agents. However, substances, which show all of these effects, i.e. substances that are active in this so-called tetrad model are considered to have affinity for the cannabinoid receptors. It has further been shown that cannabinoid receptor antagonists are highly effective in blocking the effects of a cannabinoid agonist in the mouse tetrad model.

The tetrad model is described, for example, in the publication of A. C. Howlett et al, International Union of Pharmacology XXVII. Classification of Cannabinoid Receptors, Pharmacol Rev 54, 161-202, 2002 and David R. Compton et al., "In-vivo Characterization of a Specific Cannabinoid Receptor Antagonist (SR141716A) Inhibition of Tetrahydrocannbinol-induced Responses and Apparent Agonist Activity", J. Pharmacol. Exp. Ther. 277, 2, 586-594, 1996. The corresponding parts of the description are hereby incorporated by reference.

Material and Methods

Male NMRI mice with a weight of 20-30 g (Harlan, Barcelona, Spain) are used in all of the following experiments.

Before testing in the behavioral procedures given below, mice are acclimatized to the experimental setting. Pre-Treatment control values are determined for analgesia hot plate latency (in seconds), rectal temperature, sedation and catalepsy.

In order to determine the agonistic activity of the substance to be tested, the mice are injected intravenously with the substance to be tested or the vehicle alone. 15 minutes after injection, latency in hot plate analgesia is measured. Rectal temperature, sedation and catalepsy are measured 20 minutes after injection.

In order to determine the antagonistic activity the identical procedure is used as for the determination of the agonistic effects, but with the difference that the substance to be evaluated for its antagonistic activity is injected 5 minutes before the intravenous injection of 1.25 mg/kg Win-55,212 a known cannabinoid-receptor agonist.

Hot Plate Analgesia

The hot plate analgesia is determined according to the method described in Woolfe D. et al. "The evaluation of analgesic action of pethidine hydrochloride (Demerol)", J. Pharmacol. Exp. Ther. 80, 300-307, 1944. The respective description is hereby incorporated by reference and forms part of the present disclosure.

The mice are placed on a hot plate (Harvard Analgesimeter) at 55±0.5° C. until they show a painful sensation by licking their paws or jumping and the time for these sensations to occur is recorded. This reading is considered the basal value (B). The maximum time limit the mice are allowed to remain on the hot plate in absence of any painful response is 40 seconds in order to prevent skin damage. This period is called the cut-off time (PC).

Fifteen minutes after the administration of the substance to be tested, the mice are again placed on the hot plate and the afore described procedure is repeated. This period is called the post-treatment reading (PT).

The degree of analgesia is calculated from the formula:

$$\% \text{ MPE of Analgesia} = (PT-B)/(PC-B) \times 100$$

MPE=Maximum possible effect.

Determination of Sedation and Ataxia

Sedation and ataxia is determined according to the method described in Desmet L. K. C. et al. "Anticonvulsive properties of Cinarizine and Flunarzine in Rats and Mice", Arzneim.-Forsch. (Frug Res) Sep. 25, 1975. The respective description is hereby incorporated by reference and forms part of the present disclosure.

The chosen scoring system is

0: no ataxia;

1: doubful;

2: obvious calmness and quiet;

3 pronounced ataxia;

prior to as well as after treatment.

The percentage of sedation is determined according to the formula:

$$\% \text{ of sedation} = \text{arithmetic mean}/3 \times 100$$

Hypothermia:

Hypothermia is determined according to the method described in David R. Compton et al. "In-vivo Characterization of a Specific Cannabinoid Receptor Antagonist (SR141716A) Inhibition of Tetrahydrocannbinol-induced Responses and Apparent Agonist Activity", J. Pharmacol Exp Ther. 277, 2, 586-594, 1996. The respective description is hereby incorporated by reference and forms part of the present disclosure.

The base-line rectal temperatures are determined with a thermometer (Yello Springs Instruments Co., Panlabs) and a thermistor probe inserted to 25 mm before the administration of the substance to be tested. Rectal temperature is again measured 20 minutes after the administration of the substances to be tested. The temperature difference is calculated for each animal, whereby differences of =−2° C. are considered to represent activity.

Catalepsy:

Catalepsy is determined according to the method described in Alpermann H. G. et al. "Pharmacological effets of Hoe 249: A new potential antidepressant", Drugs Dev. Res. 25, 267-282. 1992. The respective description is hereby incorporated by reference and forms part of the present disclosure.

The cataleptic effect of the substance to be tested is evaluated according to the duration of catalepsy, whereby the animals are placed head downwards with their kinlegs upon the top of the wooden block.

The chosen scoring system is:
Catalepsy for:
more than 60 seconds=6; 50-60 seconds=5, 40-50 seconds=4, 30-40 seconds=3, 20-30 seconds=2, 5-10 seconds=1, and less than 5 seconds=0.

The percentage of catalepsy is determined according ot the following formula:

% Catalepsy=arithmetic mean/6×100

III. In vivo Testing for Antiobesic Activity

The in-vivo testing for antiobesic activity of the inventive pyrazoline compounds as well as of compounds known from the prior art is carried out as described in the publication of G. Colombo et al., "Appetite Suppression and Weight Loss after the Cannabinoid Antagonist SR 141716"; Life Sciences, 63(8), 113-117, (1998). The respective part of the description is hereby incorporated by reference and forms part of the present disclosure.

The present invention is illustrated below with the aid of examples. These illustrations are given solely by way of example and do not limit the general spirit of the present invention.

EXAMPLES

Example 1

N-piperidinyl-5-(4-chlorophenyl)-1-(2,4-dichlorophenyl)-4,5-dihydro-1H-pyrazole-3-carboxamide a) 4-(4-chlorophenyl)-2-oxo-3-butenoic acid

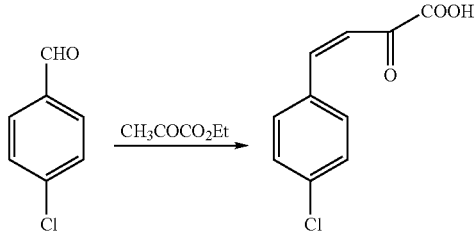

In a three neck flask p-chlorobenzaldehyde (13.3 g, 95 mmoles) and ethyl pyruvate (10 g, 86 mmoles) were dissolved in 150 ml of absolute ethanol. The solution was ice-cooled to 0° C. and an aqueous solution of NaOH (3.8 g in 45 mL water) was added dropwise keeping the temperature below or equal to 10° C., whereby a yellow-orange colored precipitate was formed. The reaction mixture was stirred for 1 hour at 0° C. and an additional 1.5 hours at room temperature (approximately 25° C.). Afterwards the reaction mixture was cooled down to approximately 5° C. and the insoluble sodium salt of 4-(4-chlorophenyl)-2-oxo-3-butenoic acid was isolated by filtration.

The filtrate was left in the refrigerator overnight, whereby more precipitate is formed, which was filtered off, combined with the first fraction of the salt and washed with diethyl ether. The sodium salt of 4-(4-chlorophenyl)-2-oxo-3-butenoic acid was then treated with a solution of 2N HCl, stirred for some minutes and solid 4-(4-chlorophenyl)-2-oxo-3-butenoic acid was separated via filtration and dried to give 12.7 g of the desired product (70% of theoretical yield).

IR (KBr, cm$^{-1}$): 3500-2500, 1719.3, 1686.5, 1603.4, 1587.8, 1081.9. $^1$H NMR(CDCl$_3$, δ): 7.4 (d, J=8.4 Hz, 2H), 7.5 (d, J=16.1 Hz, 1H), 7.6 (d, J=8.4 Hz, 2H), 8.1 (d, J=16.1 Hz, 1H).

b) 5-(4-chlorophenyl)-1-(2,4-dichlorophenyl)-4,5-dihydro-pyrazole-3-carboxylic acid

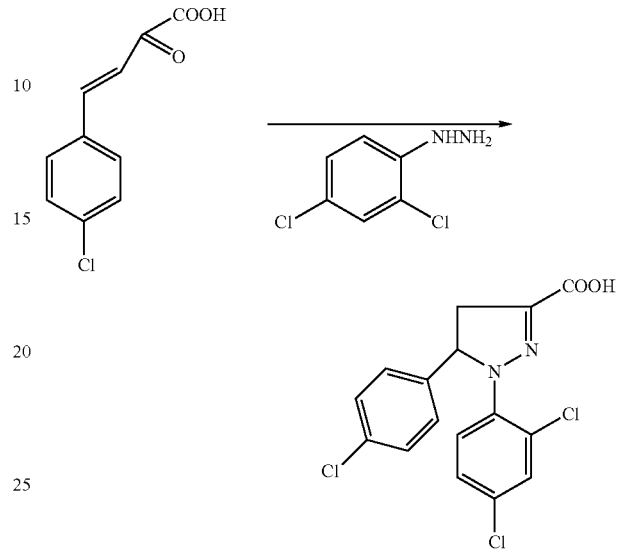

4-(4-chlorophenyl)-2-oxo-3-butenoic acid obtained according to step a) (12.6 g, 60 mmoles), 2,4-dichlorophenylhydrazine hydrochloride (12.8 g, 60 mmoles) and glacial acetic acid (200 mL) were mixed under a nitrogen atmosphere and heated to reflux for 4 hours, cooled down to room temperature (approximately 25° C.) and given into ice-water, whereby a sticky mass was obtained, which was extracted with methylene chloride. The combined methylene chloride fractions were washed with water, dried with sodium sulfate, filtered and evaporated to dryness to give a pale yellow solid (12.7 g, 57% of theoretical yield).

IR (KBr, cm$^{-1}$): 3200-2200, 1668.4, 1458, 1251.4, 1104.8. $^1$H NMR (CDCl$_3$, δ) 3.3 (dd, 1H), 3.7 (dd, 1H), 5.9 (dd, 1H), 7.09-7.25 (m, 7H).

(c) 5-(4-chlorophenyl)-1-(2,4-dichlorophenyl)-4,5-dihydro-pyrazole-3-carboxylic acid chloride

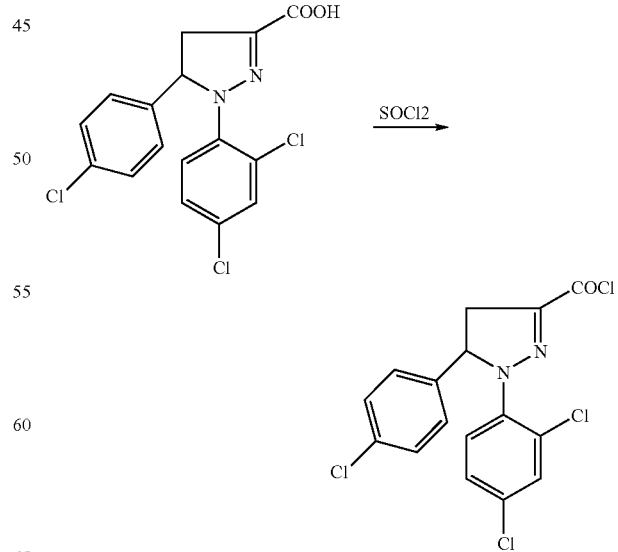

Under nitrogen atmosphere 5-(4-chlorophenyl)-1-(2,4-dichlorophenyl)-4,5-dihydro-pyrazole-3-carboxylic acid (2.5 g, 6.8 mmols) obtained according to step (b) was dissolved in 4 mL of in thionyl chloride and heated to reflux for 2.5 hours. The excess thionyl chloride is removed from the reaction mixture under reduced pressure and the resulting crude residue (2.6 g) is used without any further purification.

IR (KBr, cm$^{-1}$): 1732.3, 1700, 1533.3, 1478.1, 1212.9, 826,6.

d) N-piperidinyl-5-(4-chlorophenyl)-1-(2,4-dichlorophenyl)-4,5-dihydropyrazole-3-carboxamide

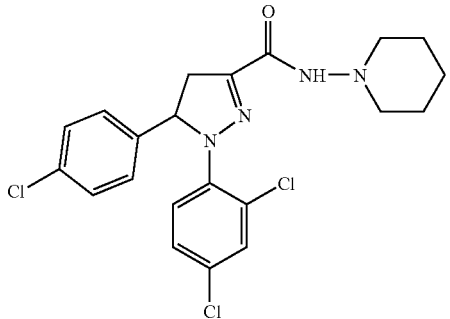

Under nitrogen atmosphere N-aminopiperidine (0.6 mL, 5.6 mmoles) and triethylamine (4 mL) were dissolved in methylene chloride (25 mL). The resulting mixture was ice-cooled down to 0° C. and a solution of 5-(4-chlorophenyl)-1-(2,4-dichlorophenyl)-4,5-dihydro-pyrazole-3-carboxylic acid chloride obtained in step (c) in methylene chloride (15 mL) was added dropwise. The resulting reaction mixture was stirred at room temperature (approximately 25° C.) overnight. Afterwards the reaction mixture was washed with water, followed by a saturated aqueous solution of sodium bicarbonate, then again with water, dried over sodium sulfate, filtered and evaporated to dryness in a rotavapor. The resulting crude solid was crystallized from ethanol. The crystallized solid was removed via filtration and the mother liquors were concentrated to yield a second fraction of crystallized product. The two fractions were combined to give a total amount of 1.7 g (57% of theoretical yield) of N-piperidinyl-5-(4-chlorophenyl)-1-(2,4-dichlorophenyl)-4,5-dihydropyrazole-3-carboxamide having a melting point of 183-186° C.

IR (KBr, cm$^{-1}$): 3222.9, 2934.9, 1647.4, 1474.7, 1268.3, 815.6. $^1$H NMR (CDCl$_3$, δ): 1.4 (m, 2H), 1.7 (m, 4H), 2.8 (m, 4H), 3.3 (dd, J=6.1 y 18.3 Hz, 1H), 3.7 (dd, J=12.5 and 18.3 Hz, 1H), 5.7 (dd, J=6.1 and 12.5 Hz, 1H), 7.0-7.2 (m, 6H), 7.4 (s, 1H).

The compounds according to the following examples 2-6 have been prepared analogously to the process described in Example 1.

Example 2

5-(4-Chloro-phenyl)-1-(2,4-dichloro-phenyl)-4,5-dihydro-1H-pyrazole-3-carboxylic acid-[1,2,4]triazol-4-yl amide Melting point: 134-138° C. IR (KBr, cm$^{-1}$): 3448, 1686, 1477, 1243, 1091, 821. $^1$H NMR(CDCl$_3$, δ): 3.1 (dd, J=6.2 and 17.9 Hz, 1H), 3.7 (dd, J=12.3 and 17.9 Hz, 1H), 5.9 (dd, J=6.2 and 12.3 Hz, 1H), 7.2-7.5 (m, 7H), 8.7 (s, 2H). 12.0 (bs, 1H).

Example 3

5-(4-Chloro-phenyl)-1-(2,4-dichloro-phenyl)-4,5-dihydron-1H-pyrazole-3-carboxylic acid-(4-methyl-piperazin-1-yl)-amide hydrochloride Melting point: 150-155° C. IR (KBr, cm$^{-1}$): 3433, 1685, 1477, 1296, 1246, 1088, 1014, 825. $^1$H NMR (CDCl$_3$, δ): 2.7 (d, J=4.2 Hz, 3H), 3.0-3.4 (m, 9H), 3.6 (dd, J=11.9 and 17.9 Hz, 1H), 5.8 (dd, J=5.5 and 11.9 Hz, 1H), 7.1 (d, J=8.4 Hz, 2H), 7.25 (2d, J=8.4 and 8.7 Hz, 3H), 7.4 (d, J=2.2 Hz, 1H), 7.5 (d, J=8.7 Hz, 1H), 9.8 (s, 1H), 11.2 (bs).

Example 4

5-(4-Chloro-phenyl)-1-(2,4-dichloro-phenyl)-4,5-dihydro-1H-pyrazole-3-carboxylic acid diethylamide This compound was obtained in form of an oil.

IR (film, cm$^-$): 2974, 1621, 1471, 1274, 1092, 820. $^1$H NMR (CDCl$_3$, δ): 1.2 (m, 6H), 3.3-3.9 (m, 6H), 5.6 (dd, J=5.8 and 11.7 Hz, 1H), 7-7.25 (m, 7H).

Example 5

[5-(4-Chloro-phenyl)-1-(2,4-dichloro-phenyl)-4,5-dihydro-1H-pyrazol-3-yl]-piperidin-1-yl-methanone Melting point: 105-110° C. IR (KBr, cm$^{-1}$) : 2934, 1622, 1470, 1446, 1266, 1010, 817. $^1$H NMR (CDCl$_3$, δ): 1.7 (m, 6H), 3.4 (dd, J=5.7 and 17.9 Hz, 1H), 3.7 (m, 3H), 3.9 (m, 2H), 5.6 (dd, J=6.1 y 11.9 Hz, 1H), 7-7.25 (m, 7H).

Example 6

N-[5-(4-Chloro-phenyl)-1-(2,4-dichloro-phenyl)-4,5-dihydro-1H-pyrazole-3-carbonyl]-4-methyl-phenyl-sulfonamide This compound was obtained in form of an amorph solid.

IR (KBr, cm$^{-1}$); 1697, 1481, 1436, 1340, 1169, 1074, 853. $^1$H NMR (CDCl$_3$, δ): 2.4 (s, 3H), 3.2 (dd, J=6.6 and 18.3 Hz, 1H), 3.6 (dd, J=12.8 and 18.3 Hz, 1H), 5.8 (dd, J=6.6 and 12.8 Hz, 1H), 7 (d, J=8.2 Hz, 2H), 7.2 (s, 1H), 7.3-7.4 (m, 6H), 8 (d, J=8.1 Hz, 2H), 9 (s, 1H).

Example 7

N-oxide of N-piperidinyl-5-(4-chlorophenyl)-1-(2,4-dichlorophenyl)-4,5-dihydropyrazole-3-carboxamide Under nitrogen gas as an inert atmosphere N-piperidinyl-5-(4-chlorophenyl)-1-(2,4-dichlorophenyl)-4,5-dihydropyrazole-3-carboxamide (0.15 g, 332 mmoles) was dissolved in 7 ml of dichloromethane. The resulting solution was ice-cooled to 0° C. and m-chloroperbenzoic acid (0.204 g, 0.83 mmoles) added in several portions. After stirring for 15 minutes a control via thin layer chromatography showed that no starting material was remaining. A saturated solution of sodium bicarbonate was then slowly added, the organic phase separated, washed with water, dried over sodium sulfate and filtered. The filtered solution was evaporated to dryness and the crude product was purified via column chromatography yielding 78 mg (50% of theoretical yield) of the N-oxide of N-piperidinyl-5-(4-chlorophenyl)-1-(2,4-dichlorophenyl)-4,5-dihydropyrazole-3-carboxamide in form of a white solid having a melting point of 115-120° C.

IR (KBr, cm$^{-1}$): 3202, 1678, 1654, 1474, 1309, 1107. $^1$H-NMR (CDCl$_3$, δ): 1.6 (m, 2H), 1.8-2.0 (m, 4H), 2.55 (m, 2H), 3.3 (dd, J=6.3 Hz and 18.2 Hz, 1H), 3.7 (m, 3H), 5.8 (dd, J=6.3 Hz and 12.5 Hz, 1H), 7.0-7.3 (m, 7H), 8.5 (s,1H.)

Pharmacological Data:

I. In-vitro Determination of Affinity to CB$_1$/CB$_2$-Rezeptors

The affinity of the inventive substituted pyrazoline compounds to CB$_1$/CB$_2$ receptors was determined as described above. Some of the values obtained are given in the following table I:

TABLE I

| Compound according to Example | CB$_1$-Receptor Radiologand: [$^3$H]-CP55940 | | CB$_2$-Receptor Radiologand: [$^3$H]-CP55940 | |
|---|---|---|---|---|
| | % Inhibition 10$^{-6}$ M | K$_i$(nM) | % Inhibition 10$^{-6}$ M | K$_i$(nM) |
| 1 | 93% | <25 | 33% | >1000 |
| 5 | 79% | 111 | 54% | ≈1000 |

As can be seen from the values given in table 1 the inventive pyrazoline compounds are particularly suitable for regulating the CB$_1$-Receptor.

II. In-vivo Bioassay System for Determination of Cannabinoid Activity

The determinination of cannabinoid activity in-vivo was determined as described above. Some of the values obtained are given in the following table II:

TABLE II

| Compound according to example: | dosis administered: 5 mg/kg i.v. Agonistic effect | | | | dosis administered 5 mg/kg i.v. prior to Win 55212-2 in a dose of 1.25 mg/kg i.v. Antagonistic Effect | | | |
|---|---|---|---|---|---|---|---|---|
| | A | B | C. | D | A | B. | C | D |
| 1 | 0 | 0 | 0 | 0 | 74 | 100 | 100 | 100 |
| 5 | 0 | 50 | 0 | 0 | 50 | 40 | 20 | 20 | i.v. intravenous
A: Hot-Plate test
B: Hypothermia
C: Catalepsy
D: Sedation

As seen from the values given in table II the inventive pyrazoline compounds act as cannabinoid receptor antagonists.

III. In-vivo Testing for Antiobesic Activity

The in-vivo testing for antiobesic activity was carried out as described above, whereby three different groups of 10 rats each were treated as follows:

Group I:
Group was treated with vehicle, namely arabic gum (5 wt.-%) in water,

Group II:
The second group of rats was treated with the inventive compound N-piperidinyl-5-(4-chlorophenyl)-1-(2,4-dichlorophenyl)-4,5-dihydropyrazole-3-carboxamide according to Example 1. Said compound was administered intraperitoneally to the rats over a period of 14 days in a daily dosis of (10 mg/kg body weight).

Group III:
The third group of rats was treated with Amphetamine, an active ingredient known to reduce appetite. Said compound was administered intraperitoneally to the rats over a period of 14 days in a daily dosis of (5 mg/kg body weight).

As can be seen from FIG. 1 the body weight is lowered due to the administration of the inventive compound according to example 1 and this effect is also observed after the treatment is ended.

Figure 2:
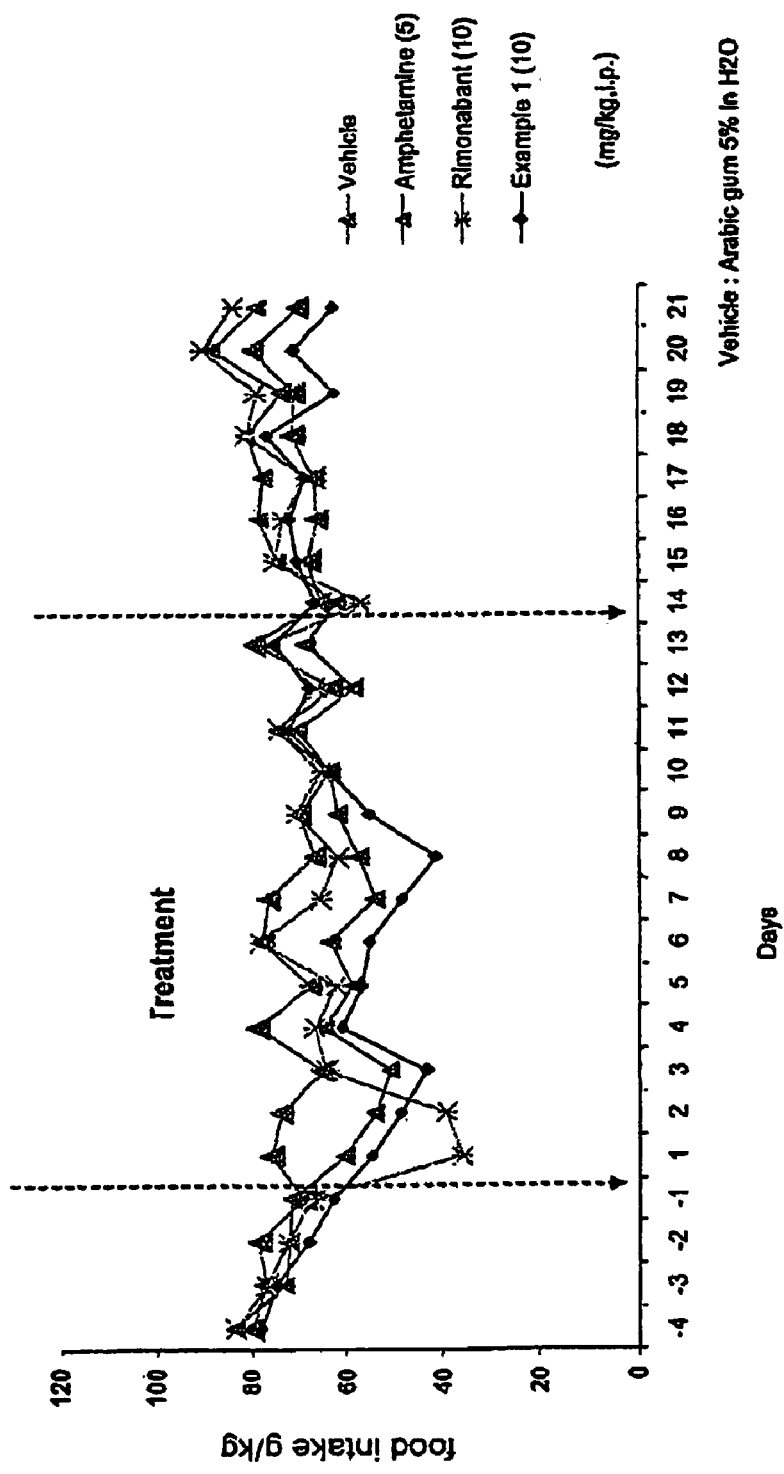

FIG. 2 shows the reduction of food intake due to the administration of the inventive compound according to example 1.

The invention claimed is:

1. N-piperidinyl-5-(4-chlorophenyl)-1-(2,4-dichlorophenyl)-4,5-dihydro-1H-pyrazole-3-carboxamide.

2. A pharmaceutical composition comprising the compound of claim 1 and a pharmaceutically acceptable excipient.

3. A method for the treatment of a food intake disorder comprising administering the compound of claim 1 wherein the disorder is selected from the group consisting of bulimia, anorexia, cachexia, obesity and type II diabetes mellitus.

* * * * *